US009733239B2

(12) United States Patent
Jiao et al.

(10) Patent No.: US 9,733,239 B2
(45) Date of Patent: Aug. 15, 2017

(54) RECONFIGURABLE MICROFLUIDIC SYSTEMS: SCALABLE, MULTIPLEXED IMMUNOASSAYS

(71) Applicants: Hong Jiao, Santa Clara, CA (US); Erik C Jensen, Berkeley, CA (US); Homayun Mehrabani, Emeryville, CA (US); Liran Yosef Haller, Berkeley, CA (US)

(72) Inventors: Hong Jiao, Santa Clara, CA (US); Erik C Jensen, Berkeley, CA (US); Homayun Mehrabani, Emeryville, CA (US); Liran Yosef Haller, Berkeley, CA (US)

(73) Assignee: HJ Science & Technology, Inc., Berkeley, CA (US)

( * ) Notice: Subject to any disclaimer, the term of this patent is extended or adjusted under 35 U.S.C. 154(b) by 145 days.

(21) Appl. No.: 14/808,939

(22) Filed: Jul. 24, 2015

(65) Prior Publication Data
US 2017/0021353 A1 Jan. 26, 2017

(51) Int. Cl.
*B01L 3/00* (2006.01)
*G01N 33/53* (2006.01)
*G01N 33/536* (2006.01)

(52) U.S. Cl.
CPC ...... *G01N 33/5302* (2013.01); *B01L 3/50273* (2013.01); *B01L 3/502738* (2013.01); *B01L 3/502746* (2013.01); *G01N 33/536* (2013.01); *B01L 2200/027* (2013.01); *B01L 2300/0864* (2013.01); *B01L 2300/0867* (2013.01); *B01L 2300/14* (2013.01); *B01L 2300/165* (2013.01); *B01L 2400/0487* (2013.01); *B01L 2400/088* (2013.01)

(58) Field of Classification Search
None
See application file for complete search history.

(56) References Cited

U.S. PATENT DOCUMENTS

| 3,993,062 | A | 11/1976 | Jess |
| 5,726,404 | A | 3/1998 | Brody |
| 6,086,825 | A | 7/2000 | Sundberg et al. |
| 6,568,910 | B1 | 5/2003 | Parce |

(Continued)

OTHER PUBLICATIONS

Oh, K. W.; Ahn, C. H., "A review of microvalves." Journal of Micromechanics and Microengineering, 2006, 16, R13.

(Continued)

*Primary Examiner* — Rebecca Martinez
(74) *Attorney, Agent, or Firm* — NUPAT, LLC; Morrison Ulman

(57) ABSTRACT

Reconfigurable microfluidic systems are based on networks of microfluidic cavities connected by hydrophobic microfluidic channels. Each cavity is classified as either a reservoir or a node, and includes a pressure port via which gas pressure may be applied. Sequences of gas pressures, applied to reservoirs and nodes according to a fluid transfer rule, enable fluid to be moved from any reservoir to any other reservoir in a system. Systems may be configured with multiple switched interaction regions connected in series for scalable, multiplexed immunoassays. Multiple, switched interaction regions may also be implemented with microvalves.

24 Claims, 35 Drawing Sheets

(56) References Cited

U.S. PATENT DOCUMENTS

| | | | |
|---|---|---|---|
| 6,811,668 | B1 | 11/2004 | Berndt et al. |
| 6,989,130 | B2 | 1/2006 | Deshmukh |
| 7,445,926 | B2 | 11/2008 | Mathies et al. |
| 7,601,270 | B1 | 10/2009 | Unger et al. |
| 7,695,603 | B2 | 4/2010 | Paul et al. |
| 8,075,854 | B2 | 12/2011 | Yang et al. |
| 8,122,901 | B2 | 2/2012 | Zeng et al. |
| 2002/0003001 | A1 | 1/2002 | Weigl et al. |
| 2002/0043463 | A1 | 4/2002 | Shenderov |
| 2002/0150512 | A1 | 10/2002 | Kellogg et al. |
| 2004/0055891 | A1 | 3/2004 | Pamula et al. |
| 2004/0109793 | A1 | 6/2004 | McNeely et al. |
| 2004/0202579 | A1 | 10/2004 | Larsson et al. |
| 2004/0228771 | A1 | 11/2004 | Zhou |
| 2005/0130292 | A1 | 6/2005 | Ahn et al. |
| 2005/0217742 | A1 | 10/2005 | Bohm |
| 2005/0255003 | A1 | 11/2005 | Summersgill |
| 2007/0075010 | A1* | 4/2007 | Gilbert .............. B01D 63/087 210/635 |
| 2007/0113908 | A1 | 5/2007 | Lee et al. |
| 2007/0166199 | A1 | 7/2007 | Zhou |
| 2008/0281090 | A1* | 11/2008 | Lee .................. B01F 11/0042 536/122 |
| 2009/0165876 | A1 | 7/2009 | Atkin et al. |
| 2011/0120562 | A1 | 5/2011 | Tan |
| 2011/0301535 | A1 | 12/2011 | Takayama et al. |
| 2014/0287966 | A1 | 9/2014 | Gray et al. |

OTHER PUBLICATIONS

Thorsen T, Maerkl SJ, Quake SR, "Microfluidic large-scale integration." Science, Oct. 18, 2002; 298 (5593) :580-4.

Unger MA, Chou HP, Thorsen T, Scherer A, Quake SR, "Monolithic microfabricated valves and pumps by multilayer soft lithography." Science, Apr. 7, 2000; 288 (5463):113-6.

WH Grover, AM Skelley, CN Liu, ET Lagally, RA Mathies, "Monolithic membrane valves and diaphragm pumps for practical large-scale integration into glass microfluidic devices." Sensors and Actuators B: Chemical 89 (3), 315-323.

Srinivasan, V; Pamula, V. K.; and Fair, R. B.; "Droplet-based microfluidic lab-on-a-chip for glucose detection." Anal. Chim. Acta., 2004, 507, 145-150.

Miller, E. M.; and Wheeler, A. R.; "A digital microfluidic approach to homogeneous enzyme assays," Anal Chem, 2008, 80, 1614-1619.

Teh, S. Y.; Lin, R.; Hung, L. H.; and Lee, A. P.; "Droplet microfluidics," Lab Chip, 2008, 8, 198-220.

DJ Harrison, A Manz, Z Fan, H Luedi, HM Widmer, "Capillary electrophoresis and sample injection systems integrated on a planar glass chip." Analytical chemistry 64 (17), 1926-1932.

Yanying Feng, Zhaoying Zhou, Xiongying Ye, Jijun Xiong, "Passive valves based on hydrophobic microfluidics," Sensors and Actuators A: Physical, vol. 108, Issues 1-3, Nov. 15, 2003, pp. 138-143.

Kim SJ, Paczesny S, Takayama S, Kurabayashi K. "Preprogrammed capillarity to passively control system-level sequential and parallel microfluidic flows." Lab Chip. Jun. 7, 2013;13(11):2091-8.

K. Ellinas, A. Tserepi, E. Gogolides, "Superhydrophobic, passive microvalves with controllable opening threshold: Exploiting plasma nanotextured microfluidics for a programmable flow switchboard", Microfluidics & Nanofluidics, DOI 10.1007/s10404-014-1335-9.

McNeely, M. R.; Spute, M. K.; Tusneem, N. A.; Oliphant, A. R. "Hydrophobic microfluidics." in Proc. SPIE, Ahn, C. H.; Frazier, A. B.; Eds.; 1999, 3877; pp. 210-220.

McNeely, M. R., Sputea, M. K., Tusneem, N. A., & Oliphant, A. R. "Sample Processing with Hydrophobic Microfluidics." JALA, 1999, 4 (4), 30-33.

Hansang Cho, Ho-Young Kim, Ji Yoon Kang, Tae Song Kim, "How the capillary burst microvalve works," Journal of Colloid and Interface Science, vol. 306, Issue 2, Feb. 15, 2007, pp. 379-385.

Daniel Irimia, "Capillary Force Valves" in Encyclopedia of Micro- and Nanofluidics edited by Li, Dongqing. 2006.

Man P F, Mastrangelo C H, Burns M A and Burke D T, "Microfabricated capillary-driven stop valve and sample injector" MEMS '98, pp. 45-50.

Yokoyama Y, Takeda M, Umemoto T and Ogushi T, "Thermal micro pumps for a loop-type micro channel," Sensors Actuators A, 2004, 111 123-8.

Melin J, Roxhed N, Gimenez G, Griss P, van der Wijngaart W and Stemme G, "A liquid-triggered liquid microvalve for on-chip flow control," Sensors Actuators B, 2004, 100 463-8.

Duffy D C, Gillis H L, Lin J, Sheppard N F and Kellogg G J, "Microfabricated centrifugal microfluidic systems: characterization and multiple enzymatic assays", Anal. Chem., 1999, 71 4669-78.

Johnson R D, Badr I H A, Barrett G, Lai S, Lu Y, Madou M J and Bachas L G, "Development of a fully integrated analysis system for ions based on ion-selective optodes and centrifugal microfluidics", Anal. Chem., 2001, 73 3940-6.

Puckett L G, Dikici E, Lai S, Madou M, Bachas L G and Daunert S, "Investigation into the applicability of the centrifugal microfluidics platform for the development of protein-ligand binding assays incorporating enhanced green fluorescent protein as a fluorescent reporter", Anal. Chem., 2004, 76 7263-8.

Leu T-S and Chang P-Y, "Pressure barrier of capillary stop valves in micro sample separators", Sensors Actuators A, 2004, 115 508-15.

Ahn C H, Choi J-W, Beaucage G, Nevin J H, Lee J-B, Puntambekar A and Lee J Y, "Disposable smart lab on a chip for point-of-care clinical diagnostics", Proc. IEEE, 2004, 92 154-73.

Yamada M and Seki M, "Nanoliter-sized liquid dispenser array for multiple biochemical analysis in microfluidic devices," Anal. Chem., 2004, 76 895-9.

Andersson H, van der Wijngaart W, Griss P, Niklaus F and Stemme G, "Hydrophobic valves of plasma deposited octafluorocyclobutane in DRIE channels," Sensors Actuators B, 2001, 75 136-41.

Andersson H, van der Wijngaart W and Stemme G, "Micromachined filter-chamber array with passive valves for biochemical assays on beads," Electrophoresis, 2001, 22 249-57.

Mosadegh B, Kuo CH, Tung YC, Torisawa YS, Bersano-Begey T, Tavana H, Takayama S., "Integrated Elastomeric Components for Autonomous Regulation of Sequential and Oscillatory Flow Switching in Microfluidic Devices," Nature Physics, Jun. 1, 2010;6(6):433-437.

James Friend, Leslie Y. Yeo, "Microscale acoustofluidics: Microfluidics driven via acoustics and ultrasonics," Rev. Mod. Phys., vol. 83, No. 2, Apr.-Jun. 2011.

Trung-Dung; Nguyen, Nam-Trung, "Surface Acoustic Wave Driven Microfluidics—A Review", Micro and Nanosystems, vol. 2(3), pp. 217-225, (2010).

International Search Report and Written Opinion of the International Searching Authority in PCT/US2016/040071, (dated Nov. 10, 2016).

* cited by examiner

+ Zero dilution steps
o One dilution step
x Two dilution steps (serial dilution)

STEP 1

STEP 2

STEP 3

STEP 4

STEP 5

RECONFIGURABLE MICROFLUIDIC SYSTEMS: SCALABLE, MULTIPLEXED IMMUNOASSAYS

GOVERNMENT LICENSE RIGHTS

This invention was made with government support under Contract Number EP-D-15-007 awarded by the United States Environmental Protection Agency. The government has certain rights in the invention.

RELATED APPLICATIONS

This application is related to "Reconfigurable microfluidic systems: Homogeneous assays", U.S. Ser. No. 14/808,929, filed on Jul. 24, 2015 and "Reconfigurable microfluidic systems: Microwell plate interface", U.S. Ser. No. 14/808,933, filed on Jul. 24, 2015.

TECHNICAL FIELD

The disclosure is generally related to microfluidic systems.

BACKGROUND

Microfluidic systems manipulate microliter and smaller scale volumes of fluids. Ink-jet printing and biochemical assays are two prominent applications of microfluidics among many others. The ability to move, control and mix tiny quantities of liquids is valuable in biochemistry since it permits more experiments to be done with a given amount of starting material. The increased surface-to-volume ratio associated with microfluidic channels as compared to traditional microwell plates also speeds up surface reactions upon which some kinds of assays are based.

Despite the profound advances in microfluidics achieved over the last 30 years, there is room for improvement. It is still a challenge, for example to make microfluidic valves that open and shut as reliably as conventional size valves. New approaches to interfaces between microfluidic devices and microwell plates are needed. Finally, microfluidic assays need to be made scalable so that hundreds or thousands of assays can be performed in parallel on one chip.

DETAILED DESCRIPTION

Reconfigurable microfluidic systems are based on networks of microfluidic cavities connected by hydrophobic microfluidic channels. Each cavity is classified as either a reservoir or a node, and includes a pressure port via which gas pressure may be applied. Sequences of gas pressures, applied to reservoirs and nodes according to a fluid transfer rule, enable fluid to be moved from any reservoir to any other reservoir in a system.

Reconfigurable microfluidic systems may be designed from these basic components—reservoirs, nodes and channels—to perform many different microfluidic tasks including homogenous and inhomogeneous assays and microwell plate interfacing. The systems are scalable to any number of fluid inputs and outputs, and they can manipulate very small fluid volumes necessary for multiplexing samples with analytes to perform multiple simultaneous assays.

A microfluidic cavity is an internal volume for accumulating fluid in a microfluidic device. A reservoir is a microfluidic cavity that is connected to only one microfluidic channel. A node is a microfluidic cavity that is connected to more than one microfluidic channel. Finally, a channel is a microfluidic passageway between nodes or reservoirs. Each channel in a reconfigurable microfluidic system connects at most two cavities. Said another way, there are no channel intersections.

Nodes are designed to present lower resistance to fluid flow than are channels. The fluid flow resistance of a cavity or channel is inversely proportional to the square of its cross sectional area. Therefore the difference in flow resistance between a channel and a reservoir, or between a channel and a node, may be engineered via different cross sectional areas.

Reservoirs store fluids; e.g. samples or reagents. Nodes, on the other hand, do not store fluid, except temporarily during a sequence of fluid transfer steps. Provisions for automated loading fluid into, or unloading fluid from, a reservoir may be provided, with a small plastic tube extending from a reservoir to a glass bottle being a simple example.

Reconfigurable microfluidic systems may be implemented in a variety of ways as long as: reservoirs, nodes, channels and pressure ports are provided; resistance to fluid flow is greater in the channels than in the nodes; and the channels are hydrophobic to prevent fluid flow when pressures at the two ends of a channel are equal or nearly so. A typical implementation includes a substrate layer, a hydrophobic fluid layer, and a pneumatic layer.

Figure 1:
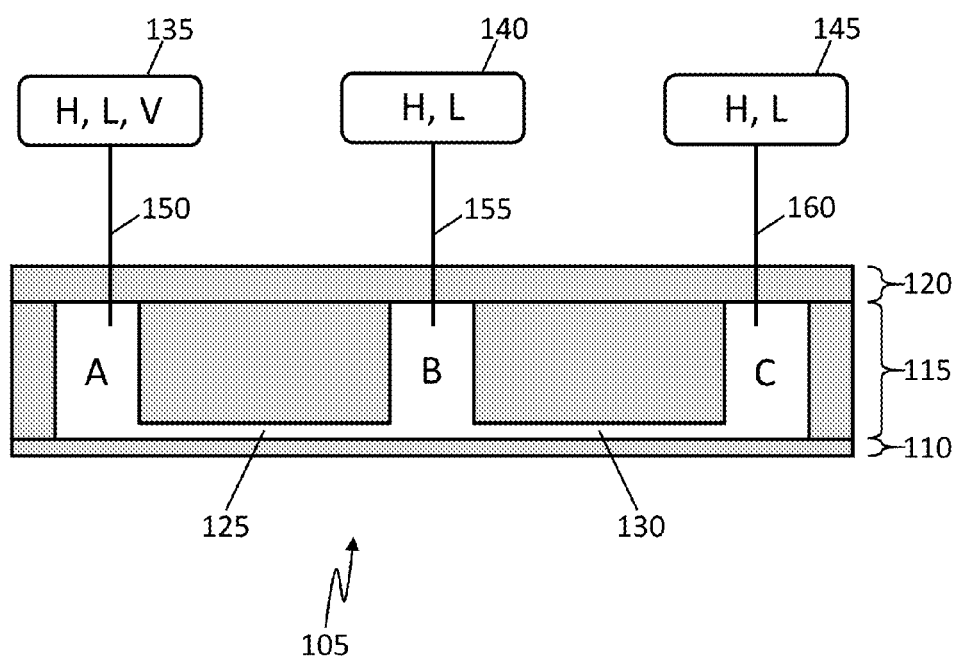
FIG. 1 is diagram of a reconfigurable microfluidic device, seen in cross section.

FIG. 1 is diagram of a reconfigurable microfluidic device, seen in cross section. In FIG. 1, microfluidic device 105 includes a substrate layer 110, a hydrophobic fluidic layer 115, and a pneumatic layer 120. Cavities in the hydrophobic fluidic layer are labeled 'A', 'B' and 'C'. Cavities A and B are connected by channel 125 while cavities B and C are connected by channel 130. Cavities A and C are classified as reservoirs because they are connected to only one channel each. Cavity B is classified as a node because it is connected to more than one channel: B is connected to both channel 125 and channel 130.

Pressure sources 135, 140 and 145 are connected to reservoir A, node B and reservoir C, respectively, via gas tubes 150, 155 and 160 respectively. Each of the three pressure sources is capable of providing at least two different pressures: a high pressure and a low pressure. Labels 'H' and 'L' in the figure refer to the capability of a pressure source to provide a high or low pressure. Pressure source 135 is also capable of providing a pressure that is less than atmospheric pressure; i.e. a partial vacuum. Label 'V' in the figure refers to this capability. As an example, high pressure may be about 2 kPa, low pressure may be about 0 kPa, and partial vacuum pressure may be about −6 kPa, where all pressures are gauge pressures.

Several different ways of making a structure like microfluidic device 105 are possible. As a first example, substrate 110 may be made of glass, polydimethylsiloxane (PDMS), polyethylene terephthalate (PET), or plastic. Hydrophobic fluidic layer 115 may be made from PDMS. A mold for casting PDMS to define hydrophobic microfluidic channels may be produced with a programmable cutter for vinyl decals or defined photolithographically in an epoxy-based negative photoresist such as SU-8. After patterned PDMS is cured and removed from a mold, it may be bonded to a flat substrate. Pneumatic layer 120 may also be made from PDMS. Gas tubes may be made from polyetheretherketone (PEEK) tubing which forms convenient seals when inserted in appropriately sized holes in PDMS. Hydrophobic materials that are suitable alternatives to PDMS include fluorinated ethylene propylene (FEP) and polytetrafluoroethylene (PTFE).

In example devices, the cross-sectional dimensions of channels 125 and 130 were about 100 µm by about 300 µm. The sizes of reservoirs A and C, and of node B were between about 2 mm and about 4 mm in diameter. The distance between reservoir A and node B was between about 5 mm and about 10 mm; the distance between node B and reservoir C was about the same. The cross-sectional areas of the cavities in typical devices are approximately 100 to 400 times greater than the cross-sectional areas of the channels. Therefore the flow resistance of the channels is about 10,000 to 160,000 times greater than the flow resistance of the cavities. Alternative designs for channels and cavities lead to the flow resistance of channels being about 100 times greater or about 1,000 times greater than the flow resistance of cavities.

A second way to make a structure like microfluidic device 105 is hot embossing a hydrophobic thermoplastic polymer such as cyclic olefin copolymer (COC) followed by solvent-assisted lamination to form enclosed, hydrophobic channels. A third way to make a structure like microfluidic device 105 is injection molding a hydrophobic polymer such as COC. Finally, hydrophilic microfluidic channels, formed in polycarbonate for example, may be made hydrophobic via chemical surface treatment. There are, no doubt, other ways to make a structure containing cavities connected by hydrophobic microfluidic channels.

Figure 2:
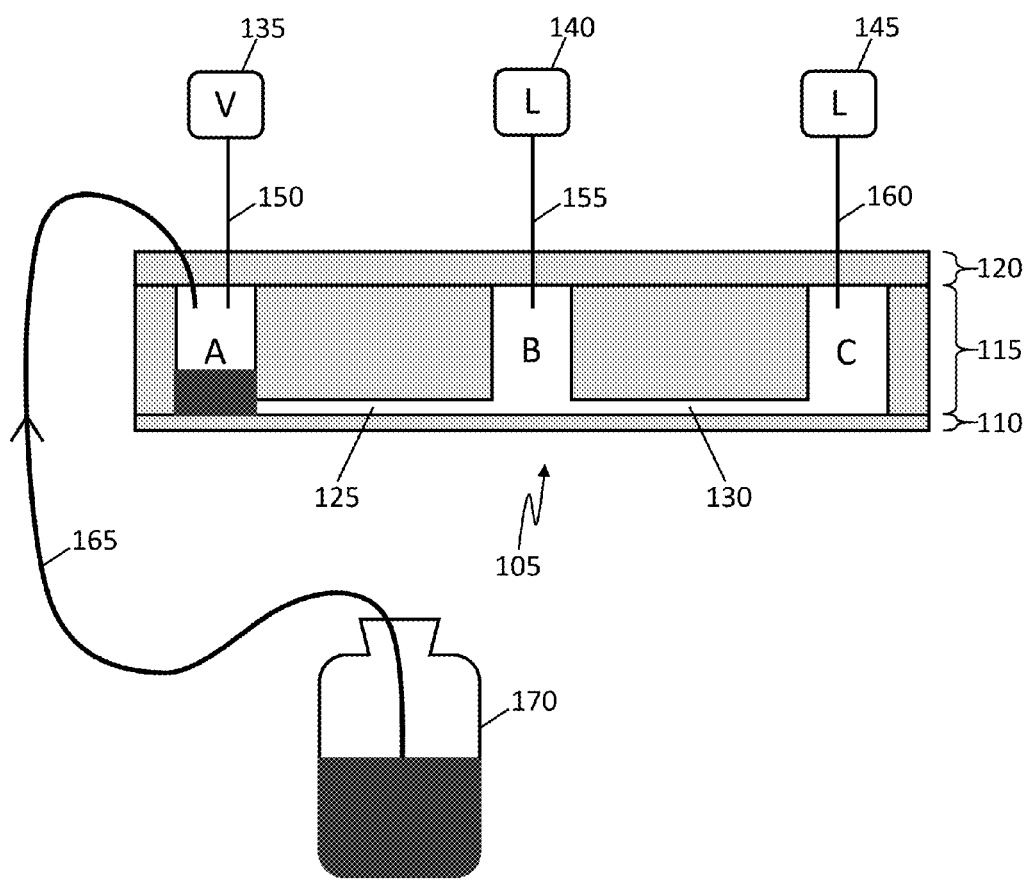
FIG. 2 illustrates loading the device of FIG. 1 from an external fluid source.

FIG. 2 illustrates loading the device of FIG. 1 from an external fluid source. In FIG. 2, reference numbers 105-160 refer to the same items as in FIG. 1. In FIG. 2, however, pressure sources 135, 140 and 145 supply partial vacuum, low pressure and low pressure, respectively. Supply tube 165 connects reservoir A to an external fluid source 170 that is at atmospheric pressure. When a partial vacuum is applied to reservoir A by pressure source 135 via gas tube 150, fluid is withdrawn from fluid source 170 and accumulated in reservoir A. Fluid does not flow from reservoir A to node B in this situation because the gas pressure applied to node B is higher than the gas pressure applied to reservoir A.

Figure 3:
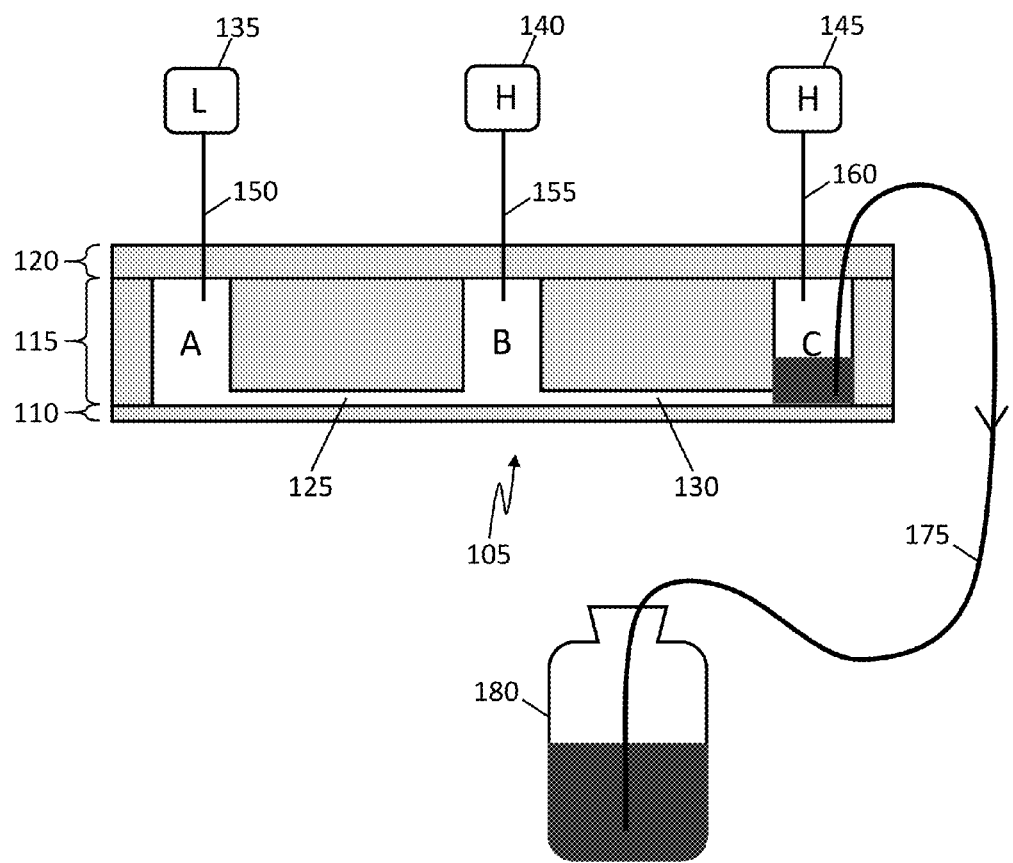
FIG. 3 illustrates unloading the device of FIG. 1 to an external fluid store.

FIG. 3 illustrates unloading the device of FIG. 1 to an external fluid store. In FIG. 3, reference numbers 105-160 refer to the same items as in FIG. 1. In FIG. 3, however, pressure sources 135, 140 and 145 supply low pressure, high pressure and high pressure, respectively. Drain tube 175 connects reservoir C to an external fluid store 180. The fluid store is at atmospheric pressure. When high pressure is applied to reservoir C by pressure source 145 via gas tube 160, fluid is expelled from reservoir C and accumulated in fluid store 180. Fluid does not flow from reservoir C to node B in this situation because the gas pressure applied to node B is the same as the gas pressure applied to reservoir C.

In reconfigurable microfluidic systems, fluid flow through microfluidic channels is controlled by gas pressure differences applied to reservoirs and nodes. Fluid flow through a hydrophobic channel exhibits a pronounced threshold effect. At first, no fluid flows as the pressure difference from one end of the channel to the other is increased. However, once a threshold pressure difference is reached, fluid flow rate through the channel increases in proportion to applied pressure difference. The hydrophobicity of channels sets the threshold pressure difference, and the difference between "high" and "low" pressures used in a system is designed to be greater than the hydrophobic threshold pressure. Thus, when the pressure is "high" at one end of a channel and "low" at the other end, fluid flows rapidly in the channel.

The hydrophobic threshold pressure of hydrophobic channels keeps fluid in nodes and reservoirs from leaking into the channels when no pressure differences are applied. The threshold pressure is designed to be great enough to prevent fluid flow that might be driven by the hydrodynamic pressure caused by the weight of fluid in a reservoir or node, or by residual pressure differences that might exist when applied pressures are switched between "high" and "low". Thus a "hydrophobic channel" is defined as one that exhibits a pressure threshold that prevents fluid from leaking into the channel when the pressure difference between the two ends of the channel is less than a design pressure. In an example reconfigurable microfluidic system, channels were designed to have about 1 kPa hydrophobic threshold pressure.

Fluid transfer between reservoirs and nodes is accomplished by switching pressures applied to each reservoir and node in a system according to a specific pattern. The following terminology aids discussion of a fluid transfer rule for reconfigurable microfluidic systems. The origin is a reservoir or node from which fluid is to be transferred. The destination is the reservoir or node to which fluid is to be transferred. Two gas pressures are needed: high pressure and low pressure.

A fluid transfer rule for reconfigurable microfluidic systems may be summarized in the following steps:

Step 0: Apply low pressure to all cavities.

Step 1: Apply high pressure to the origin and any cavity connected to the origin by a channel, other than the destination. Apply low pressure to the destination and any cavity connected to the destination, other than the origin.

Step 2 (optional): Switch origin back to low pressure. The purpose of this optional step is to ensure an air gap (i.e. section without fluid) exists in all channels after Step 1. This optional step is useful when transferring less than all of the fluid that is in the origin cavity at Step 0.

Step 3: Return to Step 0 to prepare for the next fluid transfer operation.

As explained below, the fluid transfer rule may be executed by a pressure sequencer that provides the necessary sequence of pressures to accomplish any desired fluid transfer operation. Two examples show how the fluid transfer rule is used to perform common fluid transfer experiments. The first example demonstrates flow rate control when fluid is transferred from one cavity to another; the second example demonstrates automated dilution of a fluid sample.

EXAMPLE 1

Flow Rate Control

Figure 4A:
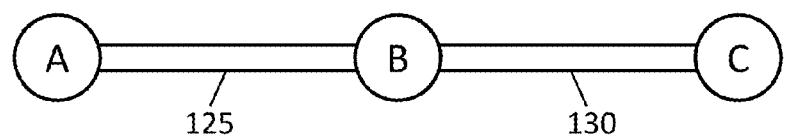
FIGS. 4A, 4B and 4C are diagrams illustrating operation of the device of FIG. 1, seen in plan view.
Figure 4B:
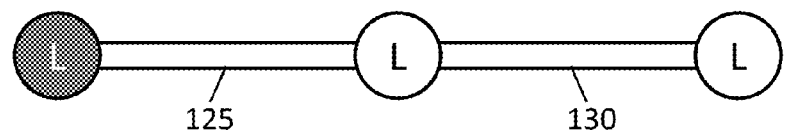
Figure 4C:
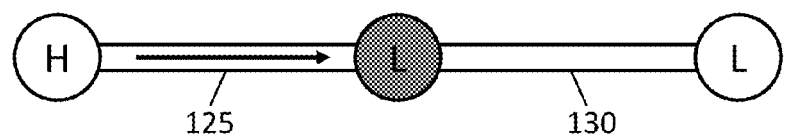

FIGS. 4A, 4B and 4C are diagrams illustrating operation of the device of FIG. 1, seen in plan view. In particular, FIG. 4A shows a plan view of reservoir A, node B and reservoir C, connected by channels 125 and 130. In FIGS. 4B and 4C, labels 'A', 'B' and 'C' are replaced by 'L', 'L' and 'L' (FIG. 4B) and 'H', 'L' and 'L' (FIG. 4C). FIG. 4A serves as a key for FIGS. 4B and 4C. 'H' and 'L' in FIGS. 4B and 4C show which cavities have high and low pressure applied to them. Shading in FIGS. 4B and 4C, and the arrow in FIG. 4C, shows that fluid moves from reservoir A to node B.

The fluid transfer rule explains how the fluid transfer depicted in FIGS. 4B and 4C is accomplished. Step 0 of the rule specifies that low pressure is applied to all cavities. FIG. 4B shows low pressure, 'L', applied to reservoir A, node B and reservoir C. Shading of reservoir A in FIG. 4B means that the reservoir has fluid in it, while node B and reservoir C are empty. Reservoir A is the origin.

Step 1 of the fluid transfer rule specifies that high pressure is applied to the origin and any cavity connected to the origin by a channel, other than the destination. Further, low pressure is applied to the destination and any cavity connected to the destination, other than the origin. This is the situation depicted in FIG. 4C. The result is fluid transfer from the origin to the destination.

All other conditions being equal, the volume of fluid transferred from the origin to the destination depends on the amount of time that pressure is applied during Step 1 of the fluid transfer rule. An experiment was conducted to demonstrate flow rate control in an apparatus similar to that shown in FIGS. 1-4.

Figure 5:
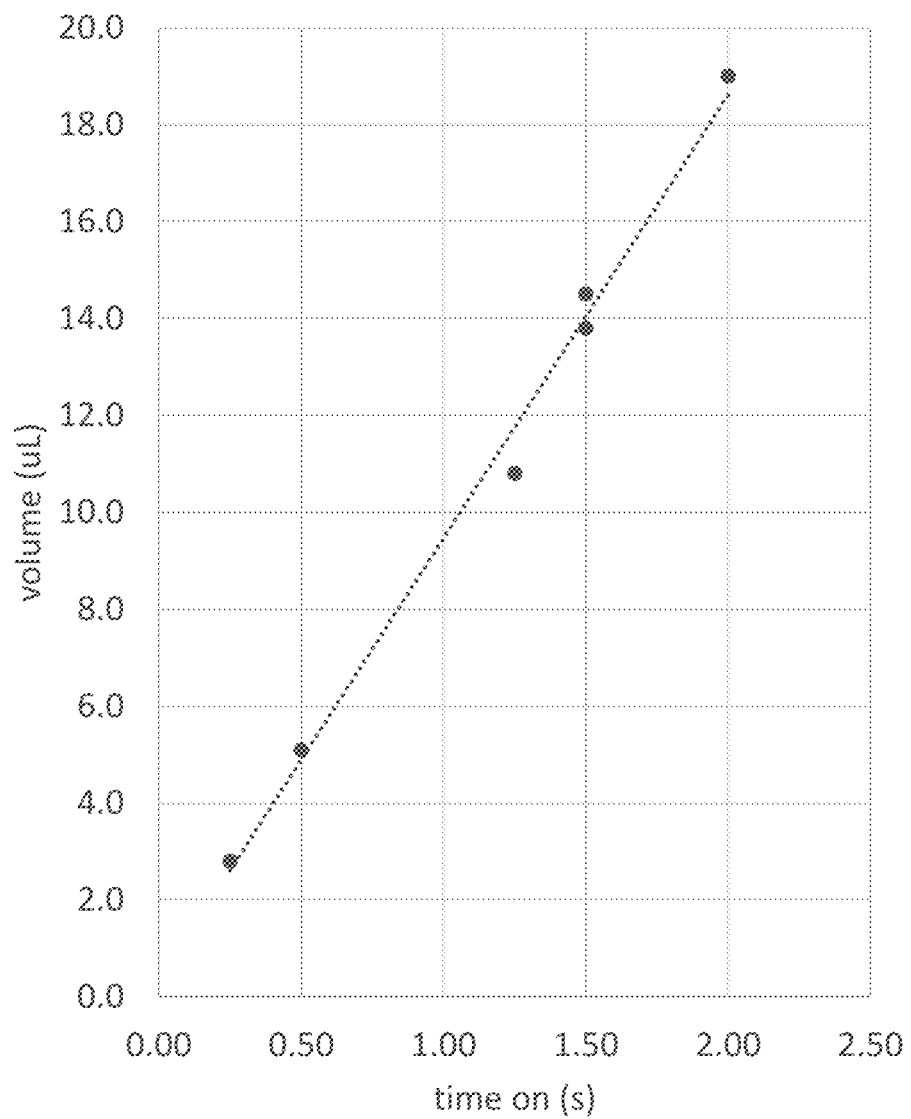
FIG. 5 is a graph of fluid volume transferred between a reservoir and a node of a device similar that of FIG. 1.

FIG. 5 is a graph of fluid volume transferred between a reservoir and a node of a device similar that of FIG. 1. The graph shows volume of fluid transferred in microliters (4) versus time (in seconds) that pressure was applied during Step 1 of the fluid transfer rule. The six black dots on the graph represent experimental data while the dashed line is a linear fit to the data. The observed flow rate is approximately 10 μL per second.

During the experiment, there was no leakage of fluid to reservoir C, even though node B and reservoir C were held at the same low pressure compared to reservoir A. Leakage to reservoir C was prevented by the high flow resistance of channel 130 compared to that of node B.

EXAMPLE 2

Automated Dilution

Figure 6:
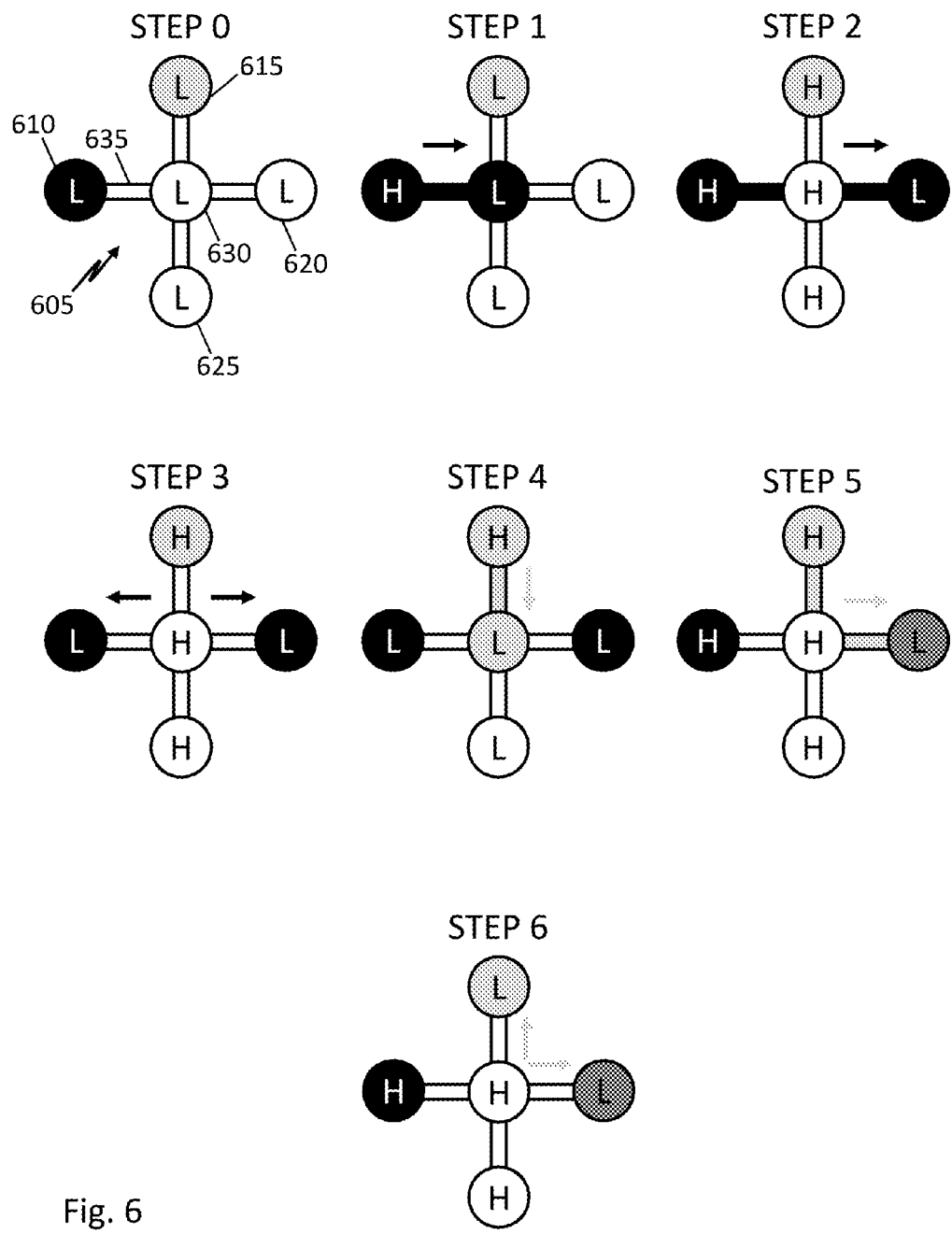
FIG. 6 is a diagram illustrating operation of a reconfigurable microfluidic device, seen in plan view.

FIG. 6 is a diagram illustrating operation of a reconfigurable microfluidic device, seen in plan view. In FIG. 6, the same device 605 is shown seven times under headings 'STEP 0', 'STEP 1', . . . , 'STEP 6'. Device 605 is similar in construction to the device of FIGS. 1-4, however device 605 has four reservoirs (610, 615, 620, 625) and one node (630). To improve visual clarity, reference numerals are not repeated for the device when it is shown under headings 'STEP 1' through 'STEP 6'. Each reservoir is connected to node 630 via its own channel. For example, channel 635 connects reservoir 610 to node 630. The other channels do not have reference numerals. The reservoirs, the channels and the node are drawn in black, gray or white during various steps. Black and gray represent two different fluids, while white represents an absence of fluid.

As discussed above, the fluid transfer rule in its basic form alternates between two states. The first state is an initial, rest condition where all cavities are at low pressure. In the second state, fluid is transferred from an origin to a destination. These two states are referred to as 'Step 0' and 'Step 1' above.

FIG. 6 uses "step" terminology. However, 'STEP 0' through 'STEP 6' in FIG. 6 are not intended to match the steps of the fluid transfer rule. Instead 'STEP 0' through 'STEP 6' are steps in an overall program during which the steps of the fluid transfer rule are applied repeatedly.

The overall result of the program shown in FIG. 6 is that some fluid from reservoir 610 is moved to reservoir 620 and some fluid from reservoir 615 is also moved to reservoir 620. Thus, at the end of the program, in 'STEP 6', reservoir 620 contains a mixture of fluids from reservoirs 610 and 615. Equivalently, reservoir 620 contains a dilution of fluid from reservoir 610 by fluid from reservoir 615.

A sequence of pressures is applied to the reservoirs and node of device 605. Pressures are indicated by labels 'H' for high pressure and 'L' for low pressure in FIG. 6. STEP 0 shows the reservoirs and node all at low pressure. Reservoirs 620 and 625, and node 630 do not contain fluid. Reservoirs 610 and 615 contain different fluids indicated by black and gray shading.

In STEP 1, high pressure is applied to origin reservoir 610 and low pressure is applied to destination node 630 and to all cavities connected to the destination, other than the origin. Fluid flows from the origin to the destination. Although not illustrated, after STEP 1, system pressures are returned briefly to the initial condition, all cavities at low pressure as in STEP 0. A reset to all cavities at low pressure occurs before and after each illustrated STEP.

In STEP 2, node 630 is the origin and reservoir 620 is the destination. Therefore high pressure is applied to the origin and all cavities connected to it, other than the destination. Low pressure is applied to the destination. Fluid flows from the origin to the destination.

STEP 3 is an example of optional Step 2 of the fluid transfer rule. The purpose of this step is to clear the channels between node 630 and reservoirs 610 and 620. An air gap must exist in a channel in order for the channel to present a hydrophobic barrier to fluid flow. Without the operation shown in STEP 3, channel 635, and the channel connecting node 630 to reservoir 620, could be left with fluid in them that would defeat their hydrophobic barriers.

In STEP 3, reservoir 610 is switched briefly back to low pressure while all other pressures remain as in STEP 2. This causes any fluid left in channel 635 to be sent back to reservoir 610. There are alternative ways to accomplish this "channel clearing" function as discussed below. Channel clearing may be needed in cases where less than all of the fluid at the origin is moved to the destination in one cycle of the fluid transfer rule.

STEP 4, STEP 5 and STEP 6 are analogous to STEP 1, STEP 2 and STEP 3 except that fluid is moved from reservoir 615 to reservoir 620 instead of from reservoir 610 to 620. Since the amount of fluid moved from one cavity to another can be controlled by the time that pressures are applied, as demonstrated in Example 1, the ratio of fluid moved to reservoir 620 from reservoir 610 to fluid moved to reservoir 620 from reservoir 615 can be adjusted at the discretion of the experimenter. Thus automated dilution may be performed by selecting an appropriate sequence of pressures to be applied to the cavities of device 605.

Figure 7:
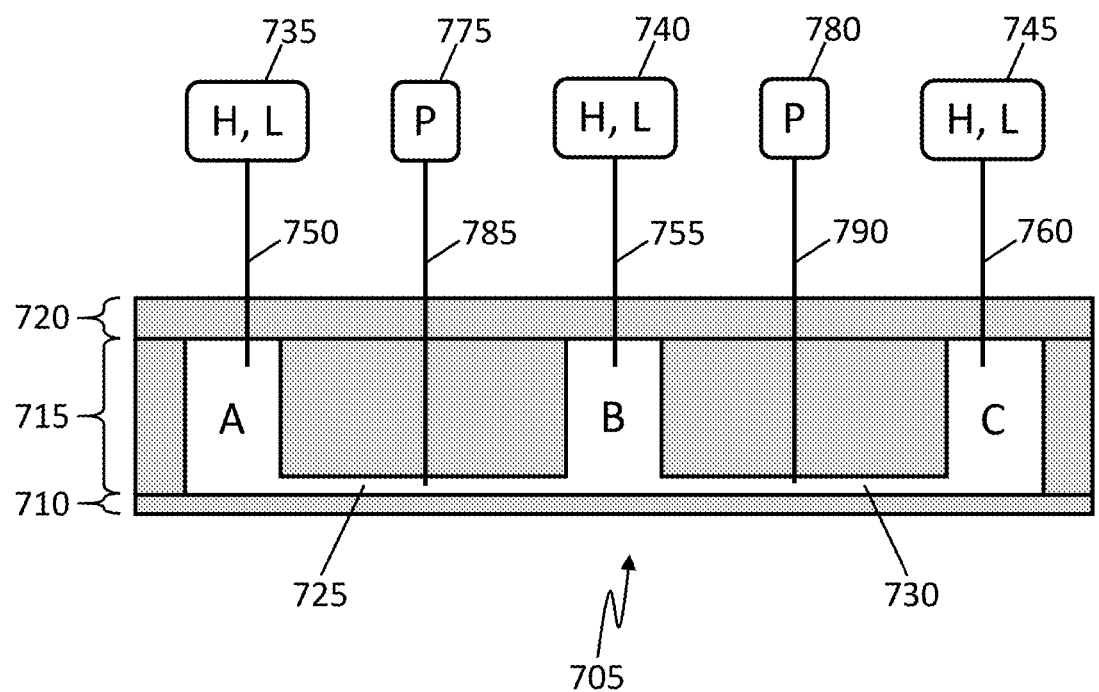
FIG. 7 is a diagram of a reconfigurable microfluidic device, seen in cross section, including ports for clearing microfluidic channels.

An alternate means for clearing out channels when only some of the fluid in an origin cavity is transferred away involves dedicated gas tubes connected to the channels. FIG. 7 is a diagram of a reconfigurable microfluidic device, seen in cross section, including ports for clearing microfluidic channels. The device of FIG. 7 is nearly the same as that of FIG. 1, except that gas tubes, pressure ports and gas pressure sources are provided to enable creation of air gaps in channels.

In FIG. 7, microfluidic device 705 includes a substrate layer 710, a hydrophobic fluidic layer 715, and a pneumatic layer 720. Cavities in the hydrophobic fluidic layer are labeled 'A', 'B' and 'C'. Reservoir A and node B are connected by channel 725 while node B and reservoir C are connected by channel 730.

Pressure sources 735, 740 and 745 are connected to reservoir A, node B and reservoir C, respectively, via gas tubes 750, 755 and 760 respectively. Each of the three pressure sources is capable of providing at least two different pressures: a high pressure and a low pressure.

Pressure sources 775 and 780 are connected to channels 725 and 730 respectively, via gas tubes 785 and 790 respectively. The gas tubes present a higher barrier to fluid flow than the channels. In normal operation of device 705 only gas, never fluid, flows in the gas tubes.

It is apparent that if device 605 of FIG. 6 were equipped with channel clearing gas tubes like gas tubes 785 and 790 of FIG. 7, then STEP 3 (optional Step 2 of the fluid transfer rule) could be replaced by a clearing STEP in which pressure is applied to channel clearing gas tubes while low pressure would be applied to all the cavities in the system.

Figure 8:
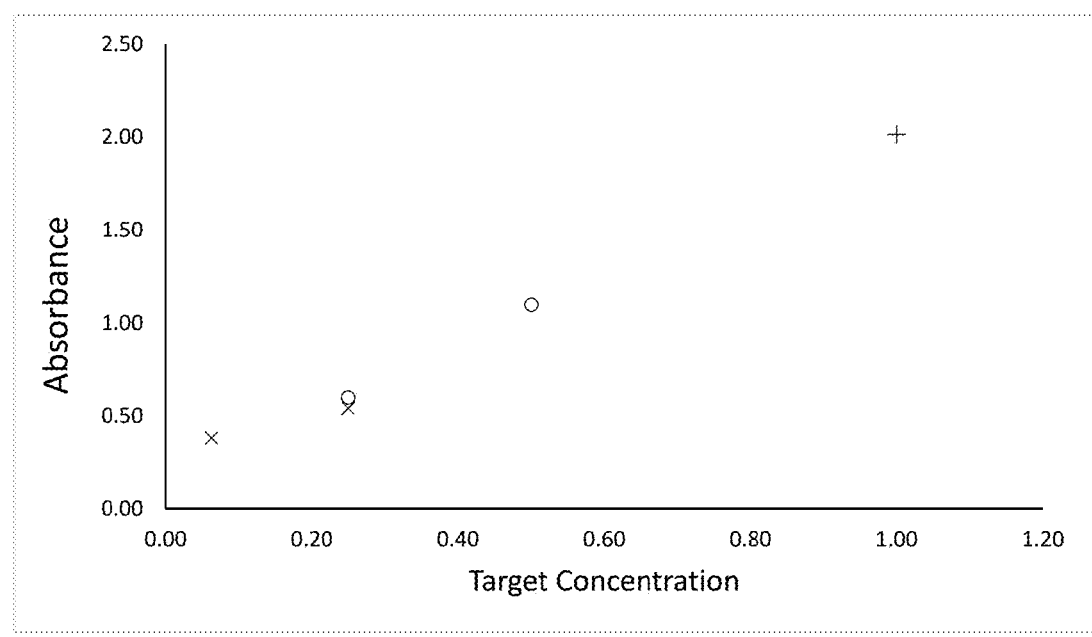
FIG. 8 is a graph of absorbance representing results of an automated dilution experiment.

An experiment was conducted to demonstrate automated dilution in an apparatus similar to that shown in FIG. 6. FIG. 8 is a graph of absorbance representing results of an automated dilution experiment. In the automated dilution experiment, concentration of an aqueous solution was inferred from optical absorbance measurements where higher absorbance corresponded to higher concentration of solute. (Optical absorbance varies linearly with concentration according to Beer's Law.) The graph in FIG. 8 therefore plots absorbance, representing measured concentration, versus target, or expected, concentration. Target concentration is an expected result if the amounts of fluid transferred into the destination reservoir from the origin solute and solvent reservoirs are as expected.

When no dilution is performed ("Zero dilution steps", "+" data point marker), absorbance 2.00 (in arbitrary units) corresponds to target concentration 1.00 (in arbitrary units). Target concentrations of 0.50 and 0.25 may be obtained in one dilution step; i.e. one time through STEPS 0 through 6 of FIG. 6. Data obtained in this way is labeled "One dilution step" and shown with "o" data point markers on the graph.

Finally data obtained after two dilution steps ("Two dilution steps (serial dilution)", "x" data point markers) is shown for target concentrations of 0.25 and 0.0625. In this case the procedure of FIG. 6 was repeated twice. Target concentration 0.25 was obtained in two ways: using one dilution step or two dilution steps. The actual concentration, as represented by absorbance data, was nearly identical in the two cases.

Figure 9:
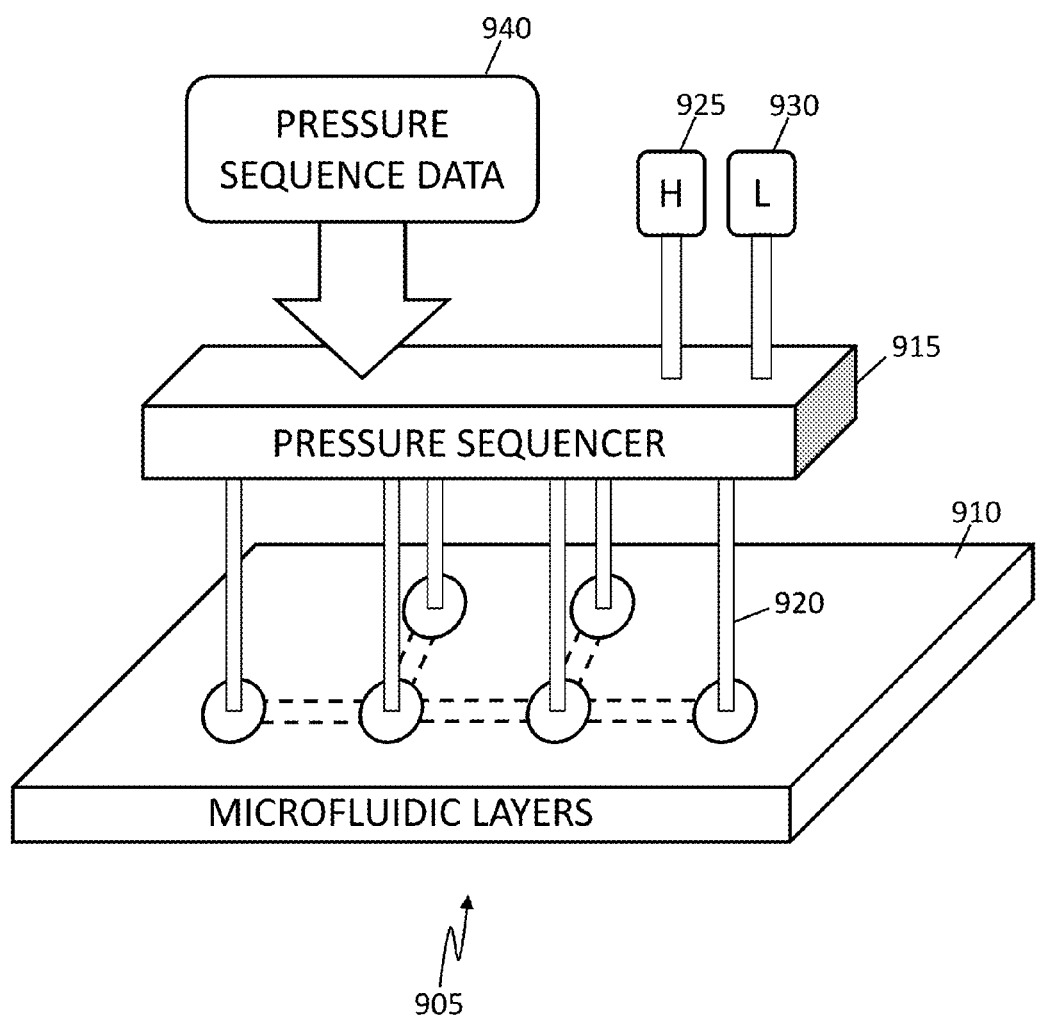
FIG. 9 is a diagram of a reconfigurable microfluidic system, including a pressure sequencer.

Examples 1 and 2 discussed above demonstrate that sequences of gas pressures, applied to reservoirs and nodes according to a fluid transfer rule, enable fluid to be moved from any reservoir to any other reservoir in a reconfigurable microfluidic system. FIG. 9 is a diagram of a reconfigurable microfluidic system 905, including a pressure sequencer 915.

In FIG. 9, microfluidic device 910 includes hydrophobic reservoirs, nodes and channels. These structures are formed in microfluidic layers of the device. Each reservoir and node is connected to pressure sequencer 915 via a gas tube, such as gas tube 920. Pressure sequencer 915 is connected to pressure sources 925 and 930. Pressure sequencer 915 includes a set of programmable gas valves.

The sequencer receives pressure sequence data 940. This data includes step by step instructions specifying what pressure is to be applied to each reservoir and node in device 910 in order to carry out a specific fluid transfer operation. As shown in Example 2, fluid can be moved from any reservoir to any other reservoir in a reconfigurable microfluidic system by repeating the steps of the fluid transfer rule.

In a laboratory experiment, pressure sequencer 915 was implemented as a set of electronically controlled pneumatic valves that were programmed using LabVIEW software (National Instruments Corporation) running on a personal computer. For the experiment, pressure sequence data necessary to move fluid from one reservoir to another in a reconfigurable microfluidic device was worked out manually. However a graphical software program may be written that allows a user to select origin and destination reservoirs, with the program then generating appropriate pressure sequence data by repeated application of the fluid transfer rule. In this way an intuitive system may be created that permits users to perform arbitrary microfluidic experiments without needing to understand the fluid transfer rule or other system operation details.

Reconfigurable microfluidic systems may have many reservoirs and nodes, especially those systems designed for parallel biochemical assays. One type of parallel assay involves performing many different biochemical experiments simultaneously on small volumes of fluid taken from one sample. A second type of parallel assay involves processing many different fluid samples simultaneously, in otherwise identical biochemical experiments. Both of these cases involve parallel operations in which groups of reservoirs or nodes change pressure together during the steps of a complex fluid transfer process.

Figure 10A:
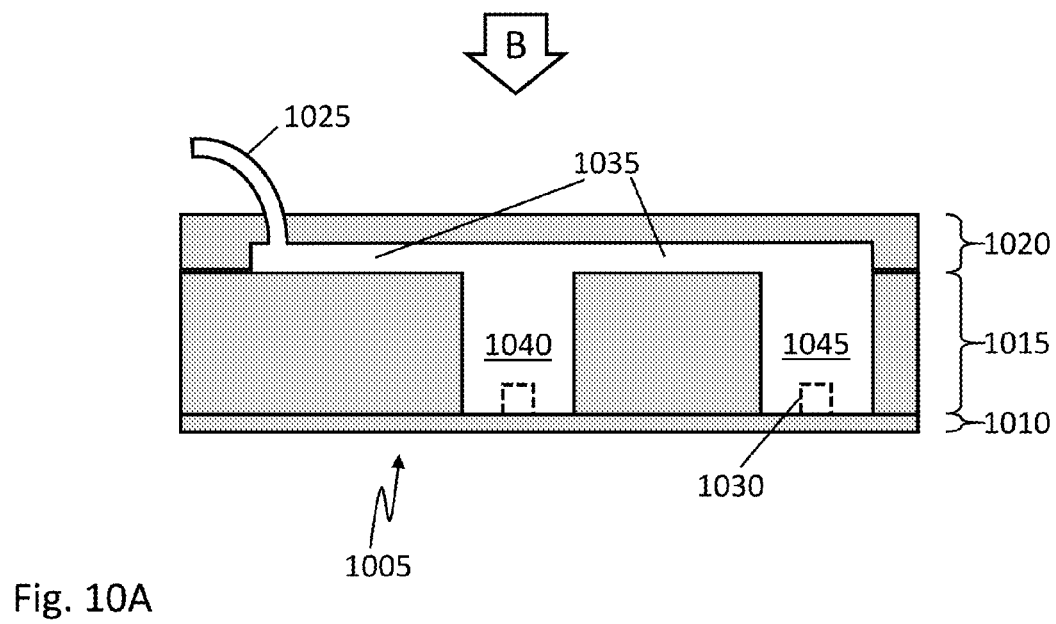
FIG. 10A (cross sectional view) and 10B (plan view) are diagrams illustrating a gas flow manifold in a reconfigurable microfluidic device.

When a reconfigurable microfluidic device has reservoirs or nodes that are operated in a group, it is more convenient to integrate a gas flow manifold in the pneumatic layer of the device than to dedicate a separate gas tube to each reservoir or node. FIG. 10A (cross sectional view) and 10B (plan view) are diagrams illustrating a gas flow manifold in a reconfigurable microfluidic device 1005.

Figure 10B:
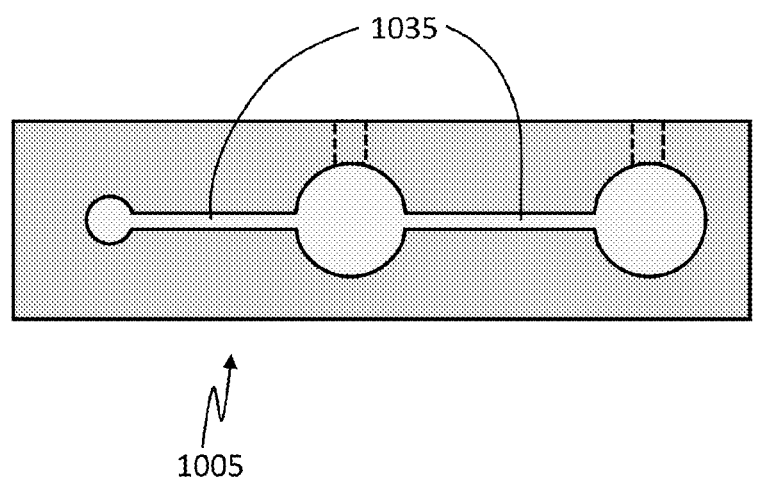

In FIG. 10A, the block arrow labeled 'B' indicates the perspective from which FIG. 10B is drawn. Device 1005 includes a substrate layer 1010, a hydrophobic microfluidic layer 1015, and a pneumatic layer 1020. Dashed lines, e.g. 1030, designate channels to microfluidic cavities that are not shown in FIG. 10A because they are not in the plane of the page. Gas tube 1025 is connected via gas flow manifold 1035 to cavity 1040 and cavity 1045. Any gas pressure supplied by the gas tube pressurizes both cavities at once. The layout of the gas flow manifold is shown in plan view in FIG. 10B. The gas flow manifold acts as a pressure port for groups of cavities that are operated in parallel.

One application for reconfigurable microfluidic devices such as those described above is scalable, multiplexed immunoassays. The immunoassays considered herein involve surface interactions. At some point in each assay, molecules are linked to a surface rather than being free floating in solution. (Such surface-interaction assays are sometimes called inhomogeneous assays.) The surface to which molecules are linked is the wall of a channel in a reconfigurable microfluidic device.

The most common immunoassays are various kinds of enzyme-linked immunosorbent assays (ELISA); however the devices and techniques described below are not limited to ELISA. On the contrary, they are applicable to any assay in which molecules are linked to a surface. Furthermore, the devices and techniques described below are applicable to surface-interaction assays that are analogous to immunoassays but do not involve antibody-antigen interactions. In these assays, a chemical species that is bound to a surface during an assay and captures another chemical species is referred to as a capture analyte. The captured species is referred to as a sample analyte. A reagent that is affected by the presence of capture-analyte-sample-analyte complexes is referred to as a detection reagent.

An immunoassay is one that involves antigen-antibody interactions. In some kinds of ELISA experiments an antigen is linked to a surface. In others, an antibody is linked to the surface. While the biochemical details of an ELISA, or other immunoassay protocol, are critically important to the scientific purpose of the particular experiment, the devices and techniques described below do not depend on these biochemical details. Thus, whenever the description mentions an antibody linked to a surface of a channel in a microfluidic device, it is understood that the same device could be employed in biochemically different kinds of experiments in which an antigen or other type of molecule is linked to a surface.

Single-channel, multichannel and multiplexed immunoassay devices are described. A single-channel assay is one that involves one kind of antibody linked to a surface and one sample. A multichannel assay is one in which many samples are processed in parallel, but with only one kind of antibody. In a multiplexed assay, experiments with many different kinds of antibodies are performed on one sample.

Multichannel and multiplexed assays may be scaled to implement assay systems that perform experiments with multiple samples and multiple antibodies. The multiplexed assay however, takes better advantage of the promise of microfluidics in terms of optimum use of small samples. In a multichannel assay, samples are loaded into each channel from a "macrofluidic" device, such as a pipette robot. In a multiplexed assay, however, a single sample is routed via microfluidic channels for testing with different kinds of antibodies.

The multiplexed assays described below depend on a microfluidic switched interaction region which is implemented in a reconfigurable microfluidic device. Multiplexing is achieved by arranging multiple microfluidic switched interaction regions in series. A switched interaction region may also be implemented in a microfluidic device having conventional microvalves, albeit with increased complexity.

FIGS. 11-16 are diagrams of a reconfigurable microfluidic device for single channel immunoassays, seen in plan view. FIGS. 11-16 outline steps in a single-channel immunoassay; i.e. an assay that involves one antibody linked to a surface and one sample. In FIGS. 11-16, reconfigurable microfluidic device 1105 includes: reservoirs 1110, 1115, 1120, 1125, 1130, 1145 and 1150; nodes 1135 and 1140; and channels 1155, 1160, 1165 and 1170. Other channels, such as the channel connecting reservoir 1115 to node 1135, are not labeled with reference numbers.

Figure 11:
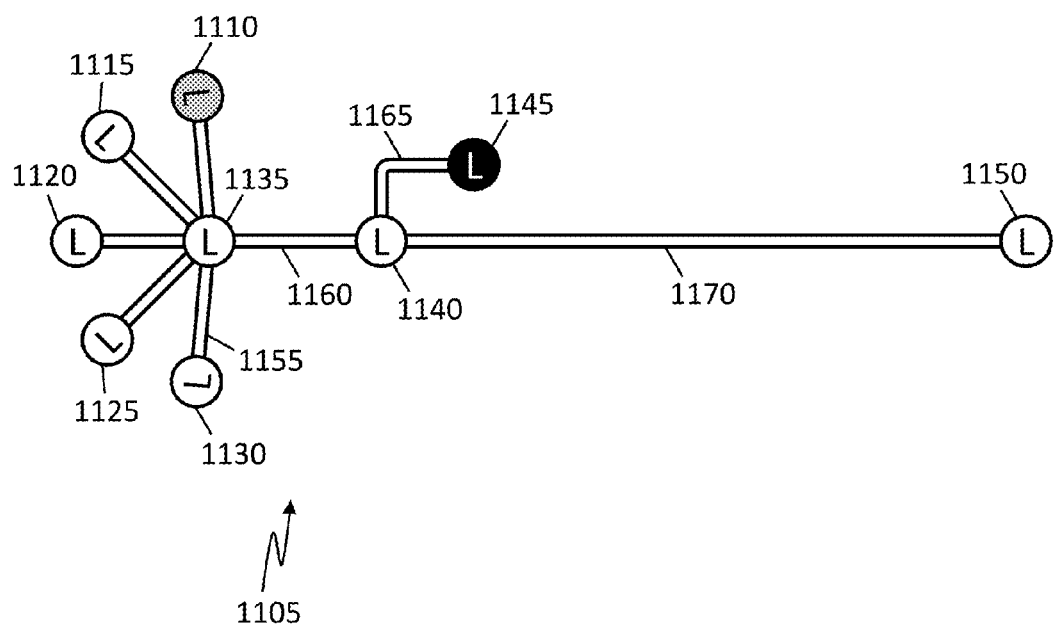
FIG. 11 is a diagram of a reconfigurable microfluidic device for single channel immunoassays, seen in plan view.

Device 1105 may be constructed in layers exactly as described above; it is only the layout of reservoirs, nodes and channels that is different. The plan view shown in FIG. 11 is analogous to that of FIG. 4. A corresponding cross-sectional view of the device of FIG. 11 is not provided, but would essentially be a more complicated version of FIG. 1. Channel 1170 is intentionally designed longer than the other channels as it serves as an interaction region where antigen-antibody biochemical reactions take place.

In an example ELISA experiment, reservoirs 1110, 1115, 1120, 1125, 1130 contained wash buffer (e.g. phosphate buffered saline with Tween 20, "PBST"), horse radish peroxidase ("HRP") conjugate, 3,3',5,5'-Tetramethylbenzidine substrate ("TMB"), microcystin antibody, and blocking buffer (e.g. SuperBlock™ (Life Technologies) or equivalent), respectively. Of course, it does not matter which reservoir contained what solution, only that each solution had its own reservoir. Reservoir 1145 contained a sample solution containing microcystin target antigen.

Figure 15:
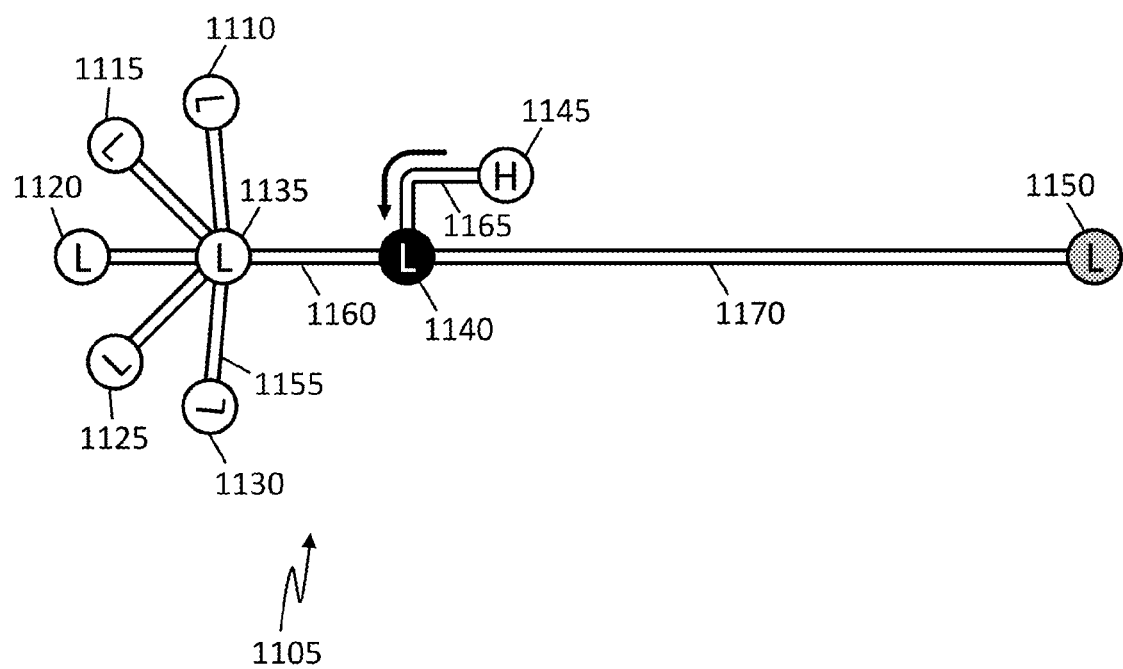
FIG. 15 is a diagram of a reconfigurable microfluidic device for single channel immunoassays, seen in plan view.
Figure 16:
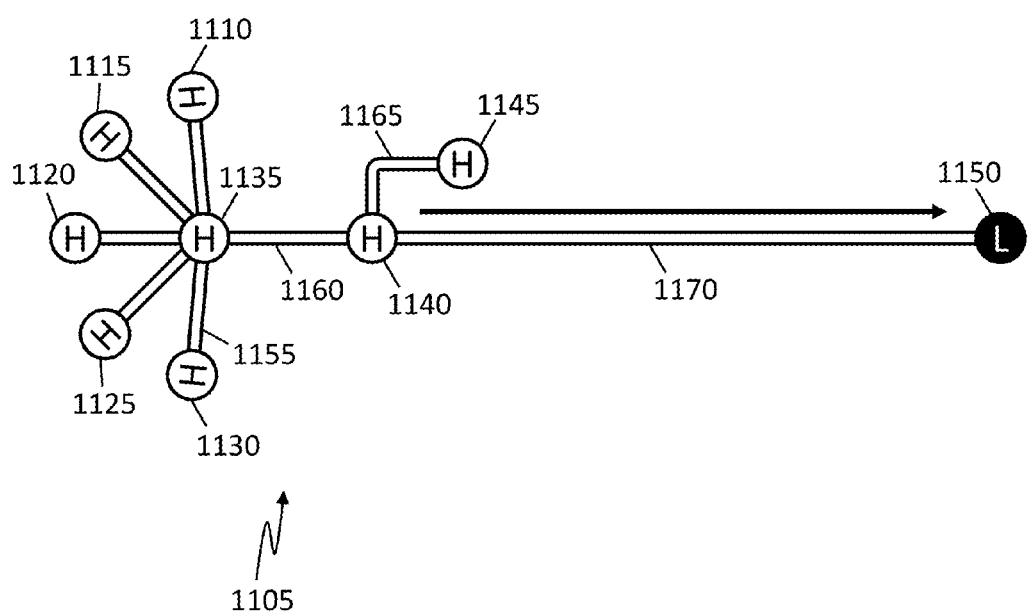
FIG. 16 is a diagram of a reconfigurable microfluidic device for single channel immunoassays, seen in plan view.

The example experiment involves coating the interaction region (channel 1170) with antibody, followed by wash buffer, blocking buffer, wash buffer, sample incubation, HRP incubation, wash buffer, and TMB substrate incubation steps. FIGS. 11-14 show steps in which a solution from one of reservoirs 1110, 1115, 1120, 1125, 1130 is transferred to reservoir 1150 via the interaction region, channel 1170. FIGS. 15 and 16 show steps in which sample solution is transferred from reservoir 1145 to reservoir 1150 via interaction region 1170.

FIGS. 11-16 are labeled 'STEP 0', 'STEP 1' . . . 'STEP 5'. The change in configuration from 'STEP 0' to 'STEP 1', and from 'STEP 1' to 'STEP 2', etc., is accomplished by applying pressures to the reservoirs and nodes of device 1105 according to the fluid transfer rule. In FIGS. 11-16, 'L' and 'H' indicate either low or high pressure, respectively, applied to a reservoir or node.

Figure 12:
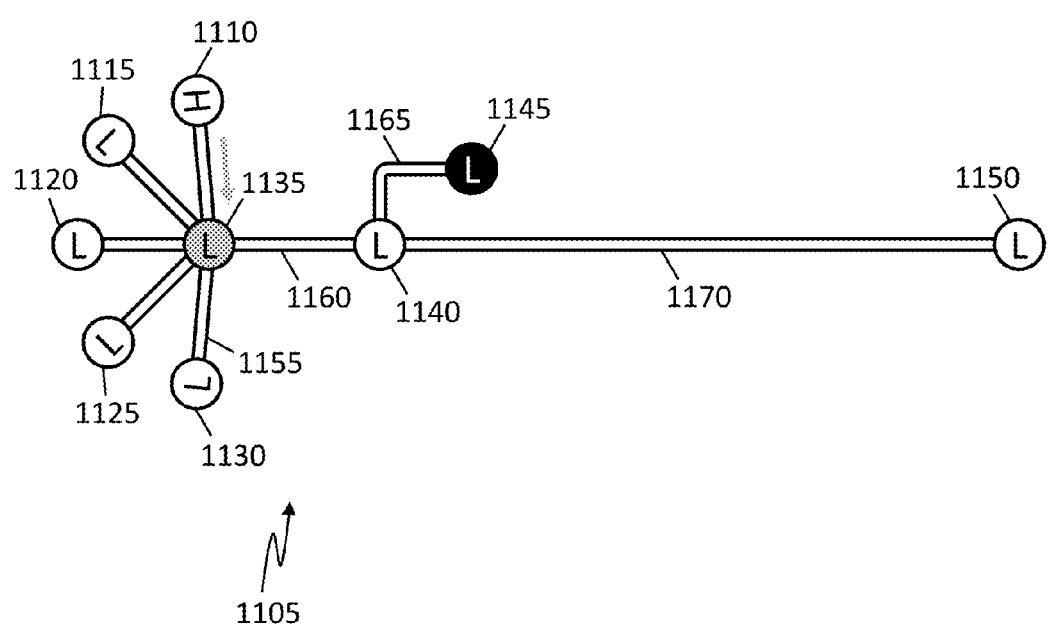
FIG. 12 is a diagram of a reconfigurable microfluidic device for single channel immunoassays, seen in plan view.
Figure 13:
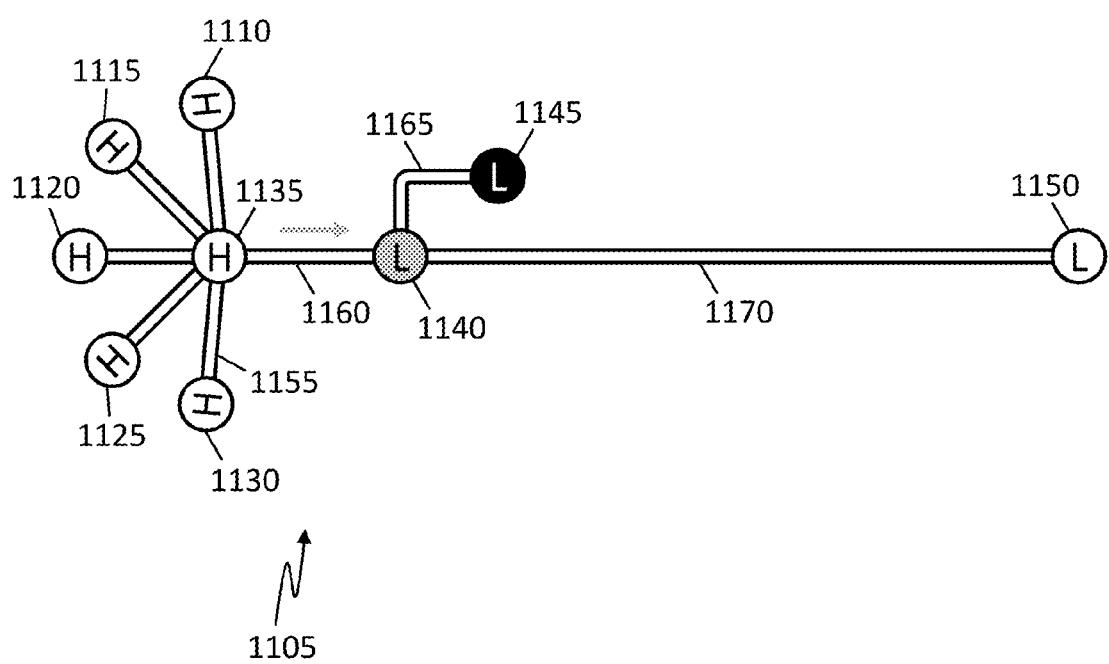
FIG. 13 is a diagram of a reconfigurable microfluidic device for single channel immunoassays, seen in plan view.

FIG. 11, STEP 0, is the initial condition in which all reservoirs and nodes are at low pressure. Shading highlights the presence of fluid in reservoirs 1110 and 1145. In FIG. 12, STEP 1, fluid from reservoir 1110 is transferred to node 1135. In FIG. 13, STEP 2, fluid from node 1135 is transferred to node 1140.

Figure 14:
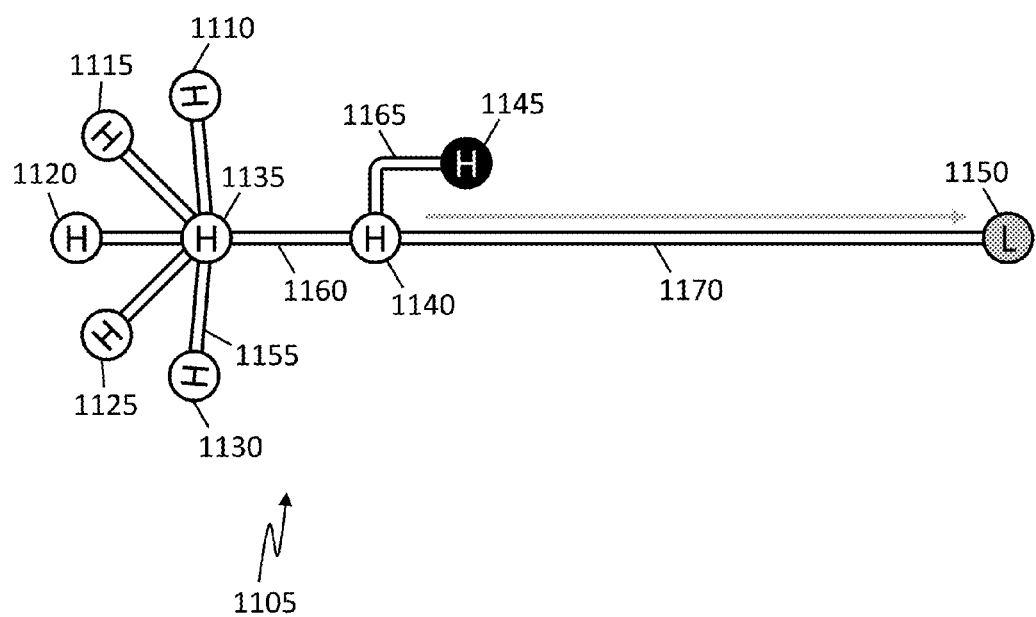
FIG. 14 is a diagram of a reconfigurable microfluidic device for single channel immunoassays, seen in plan view.

In FIG. 14, STEP 3, fluid from node 1140 is transferred to reservoir 1150. In an actual immunoassay experiment, this step is completed in two stages: first, fluid is pushed from node 1140 into channel 1170 and allowed to incubate there; second the fluid is pushed into reservoir 1150. This procedure permits, for example, coating the walls of channel 1170 with antibodies or incubation of a sample with antibodies that have been chemically linked to the walls of the channel in a previous step.

In FIG. 15, STEP 4, sample solution from reservoir 1145 is transferred to node 1140. In FIG. 16, STEP 5, the sample solution is transferred from node 1140 to reservoir 1150. As in STEP 3, this transfer is completed in two stages in an actual immunoassay, including incubation time in channel 1170.

Figure 17:
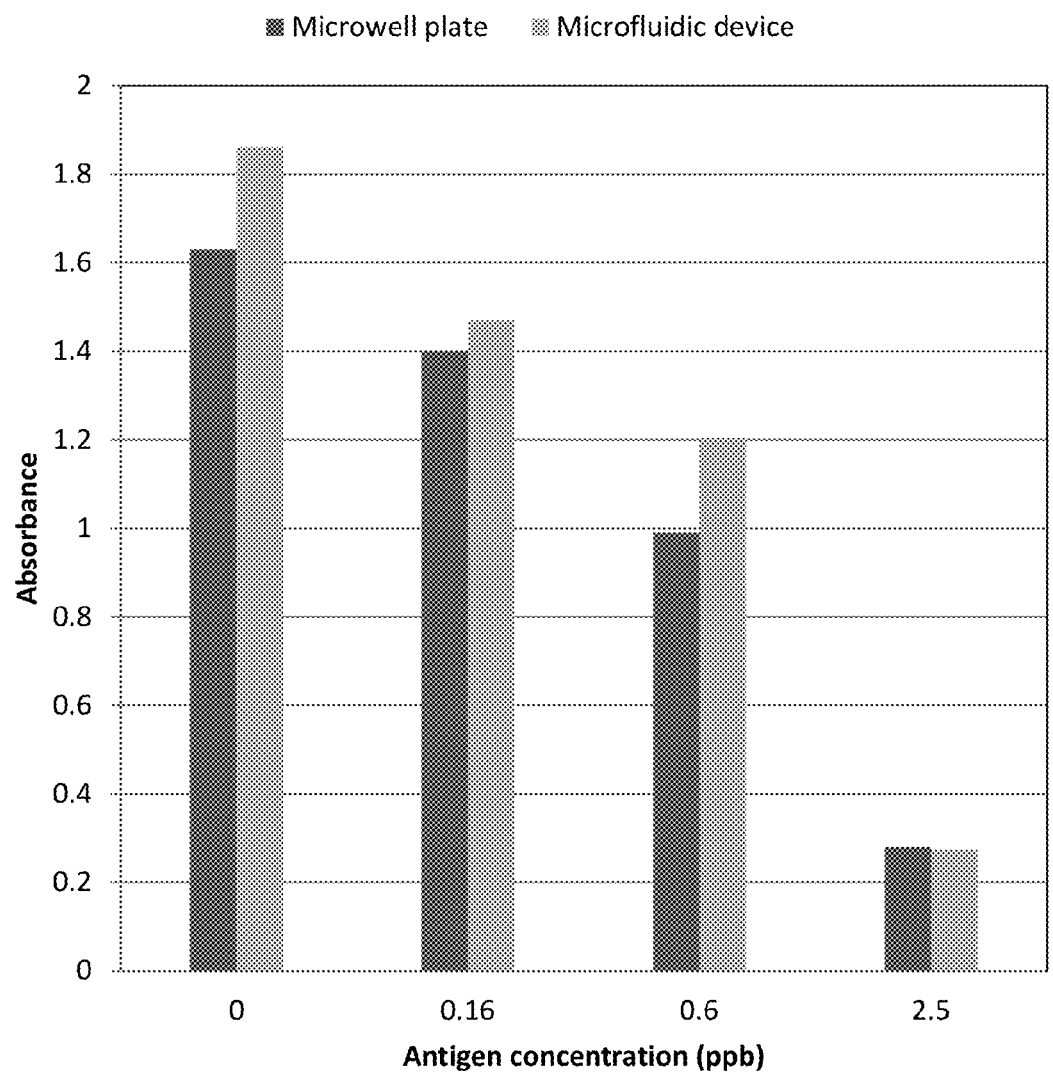
FIG. 17 is a graph of competitive ELISA absorbance data.
Figure 18:
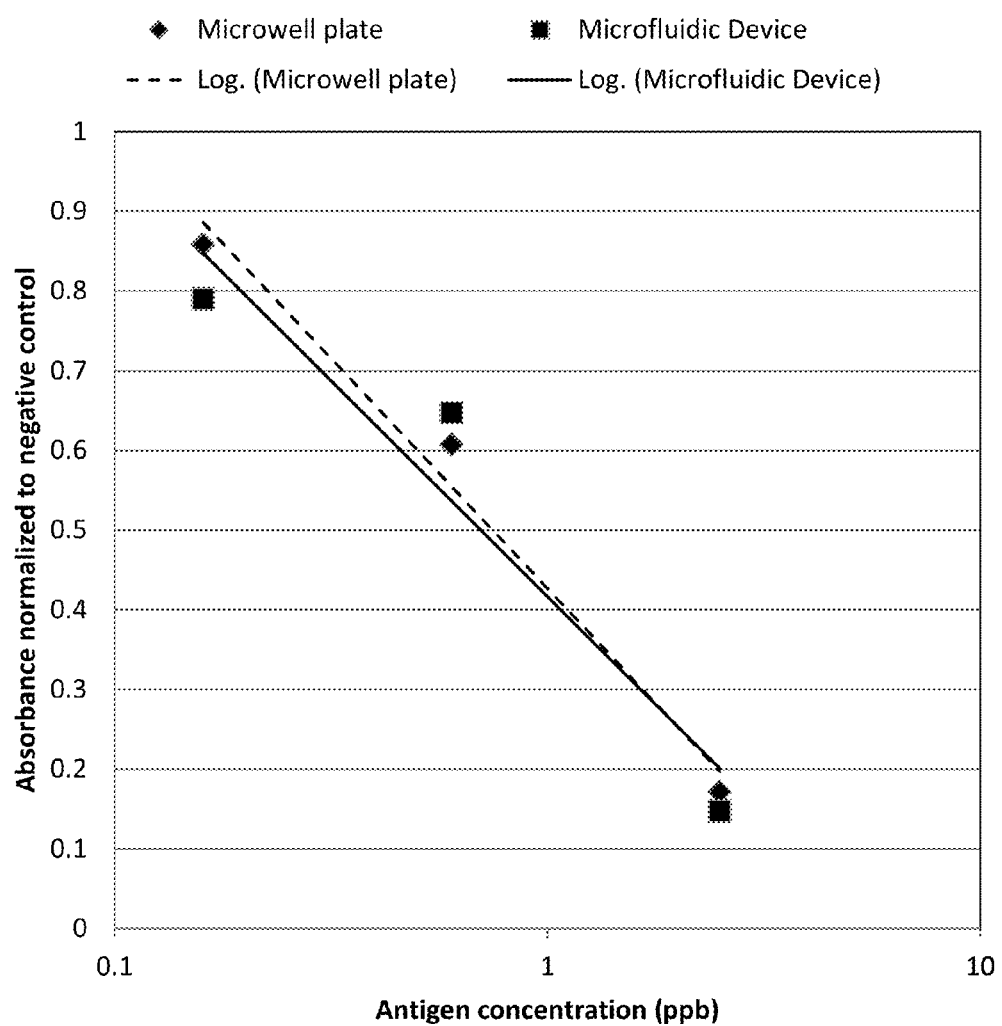
FIG. 18 is a graph of competitive ELISA normalized absorbance data.

Results from the single-channel ELISA experiment outlined in FIGS. 11-16 are presented in FIGS. 17 and 18 which are graphs of competitive ELISA absorbance data. FIGS. 17 and 18 compare ELISA results from the biochemical assay performed in the device of FIGS. 11-16 with results from the same biochemical assay performed in a standard 96-well plate.

The assay performed in the reconfigurable microfluidic device used only about 15% of the sample, enzyme and substrate volumes that the 96-well plate version required. Not including antibody coating, the assay in the microfluidic format took 29 minutes versus 94 minutes for the 96-well plate assay. (The 96-well plate assay kit comes with antibodies pre-coated on the plate. Antibody coating took 23 minutes in the microfluidic format.) A competitive ELISA has been demonstrated and extensions to other kinds of ELISA, such as sandwich ELISA, are straightforward.

FIG. 17 is a graph of optical absorbance (arbitrary units) versus antigen concentration (parts per billion) in a sample for a competitive ELISA experiment performed in a 96-well plate (darker shaded data bars) and for the same experiment performed in the reconfigurable microfluidic device of FIGS. 11-16. There is good agreement among the data for the two assay formats.

FIG. 18 is a graph of optical absorbance normalized to absorbance measured for a negative control; i.e. an experiment where the concentration of antigen was zero. Diamond and square data markers correspond to data obtained in a 96-well plate assay and a microfluidic device format, respectively. The dashed line is a logarithmic fit to the 96-well plate data while the solid line is a logarithmic fit to the microfluidic device data. There is good agreement among the data for the two assay formats.

The single channel immunoassay device just described may be extended for multichannel operation. FIGS. 19-24 are diagrams of a reconfigurable microfluidic device for multichannel immunoassays, seen in plan view. FIGS. 19-24 outline steps in a multichannel immunoassay; i.e. an assay that involves many samples and one surface-linked antibody. In FIGS. 19-24, reconfigurable microfluidic device 1905 includes: reservoirs 1910, 1915, 1920, 1925, 1930, 1945 and 1950; nodes 1935 and 1940; and channels 1955, 1960, 1965 and 1970. Other channels, such as the channel connecting reservoir 1915 to node 1935, are not labeled with reference numbers. Structures that are duplicated from one immunoassay experiment to the next are also not labeled with reference numbers. The volume of node 1935 is about eight times larger than the corresponding node 1135 in FIG. 11.

Although it is clear in context, a distinction should be kept in mind between a "multichannel" immunoassay and a microfluidic device having two or more, i.e. "multiple", microfluidic channels. Every microfluidic device discussed herein has more than one microfluidic channel. (If a device had only one microfluidic channel, it would also have only two reservoirs and no nodes, and probably would not be very useful.) In the context of immunoassays, "multichannel" means that more than one immunoassay experiment is performed simultaneously. Each experiment is performed in an experimental "channel" of a multichannel device. Device 1905 has 29 microfluidic channels and eight immunoassay experimental channels. Dashed rectangle 1975 encloses one immunoassay channel, for example.

Figure 19:
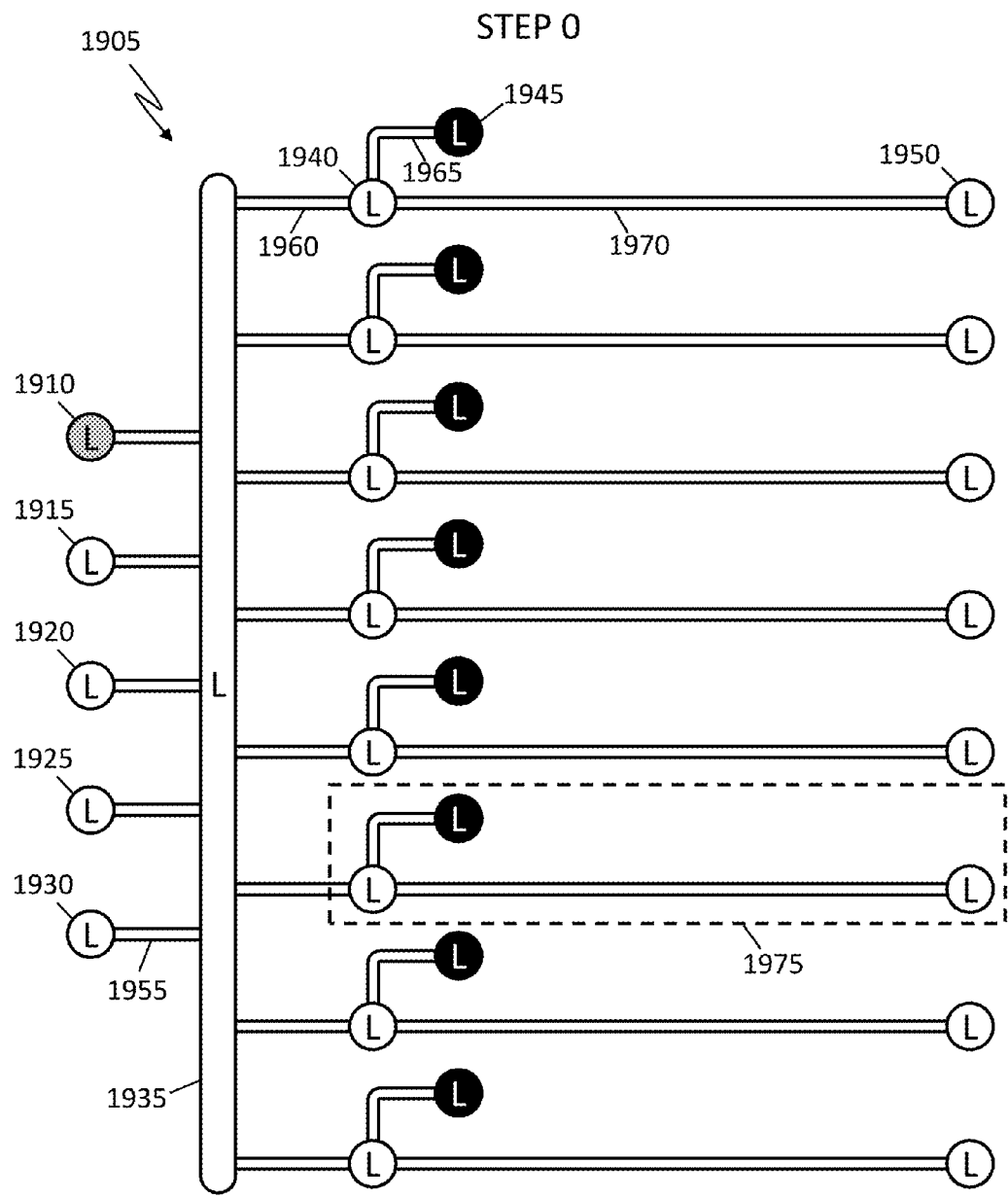
FIG. 19 is a diagram of a reconfigurable microfluidic device for multichannel immunoassays, seen in plan view.

Device 1905 may be constructed in layers exactly as described above; it is only the layout of reservoirs, nodes and channels that is different. The plan view shown in FIG. 19 is analogous to that of FIG. 4. A corresponding cross-sectional view of the device of FIG. 19 is not provided, but would essentially be a more complicated version of FIG. 1. Channel 1970 is intentionally designed longer than the other channels as it serves as an interaction region where antigen-antibody biochemical reactions take place.

As an example, a multichannel ELISA may be performed with reservoirs 1910, 1915, 1920, 1925, 1930 containing PBST, HRP conjugate, TMB, microcystin antibody, and blocking buffer, respectively. Of course, it does not matter which reservoir contains what solution, only that each solution has its own reservoir. Reservoir 1145 contains a sample solution and each corresponding reservoir in the eight immunoassay channels may contain its own, different sample solution.

Figure 23:
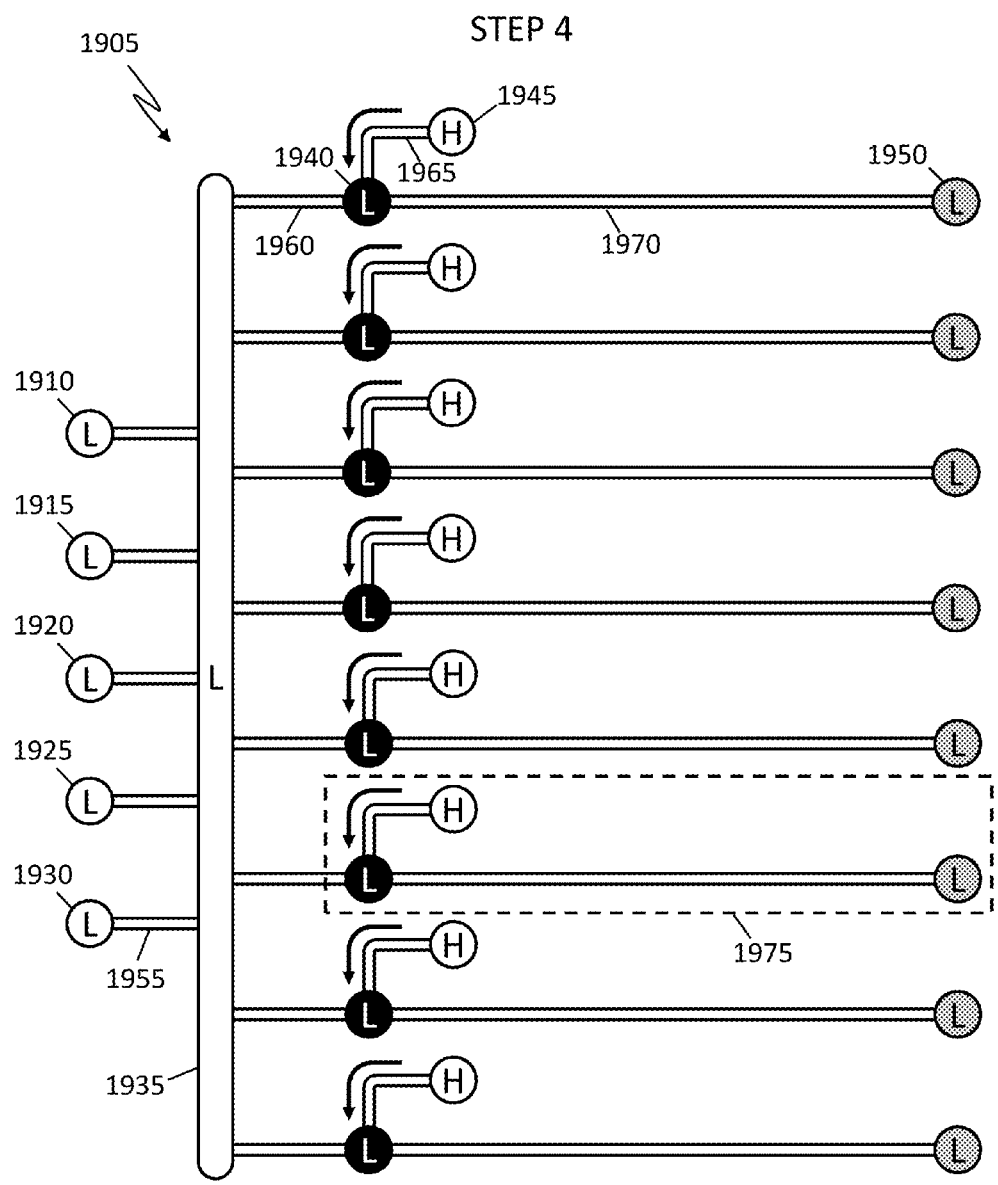
FIG. 23 is a diagram of a reconfigurable microfluidic device for multichannel immunoassays, seen in plan view.
Figure 24:
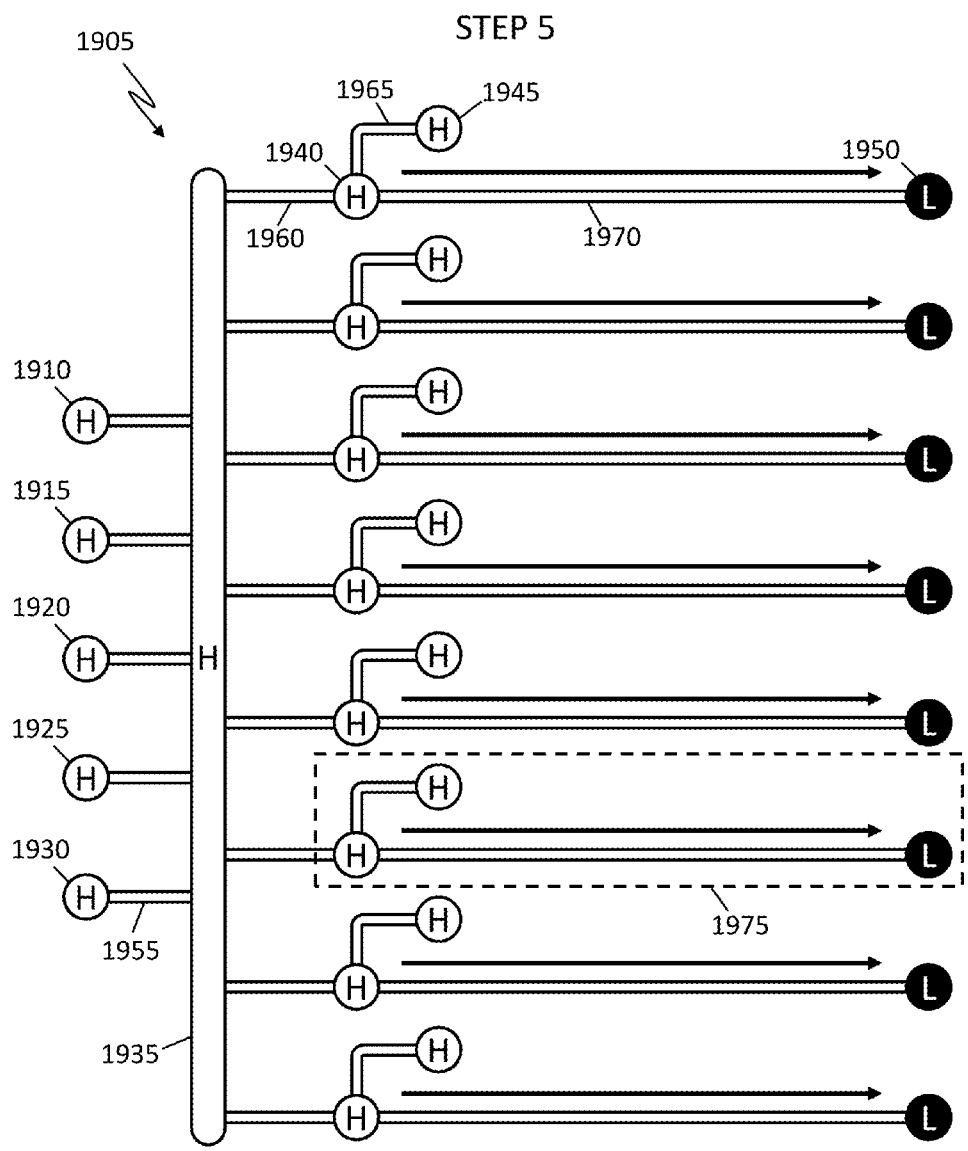
FIG. 24 is a diagram of a reconfigurable microfluidic device for multichannel immunoassays, seen in plan view.

Multichannel ELISA involves coating the interaction region (channel 1970) with antibody, followed by wash buffer, blocking buffer, wash buffer, sample incubation, HRP incubation, wash buffer, and TMB substrate incubation steps. FIGS. 19-22 show steps in which, for example, a solution from one of reservoirs 1910, 1915, 1920, 1925, 1930 is transferred to reservoir 1950 via the interaction region, channel 1970. These steps are performed simultaneously on all eight immunoassay channels. FIGS. 23 and 24 show steps in which, for example, sample solution is transferred from reservoir 1945 to reservoir 1950 via interaction region 1970. These steps are performed simultaneously on all eight immunoassay channels, each with its own, possibly different, sample solution.

FIGS. 19-24 are labeled 'STEP 0', 'STEP 1' . . . 'STEP 5'. The change in configuration from 'STEP 0' to 'STEP 1', and from 'STEP 1' to 'STEP 2', etc., is accomplished by applying pressures to the reservoirs and nodes of device 1905 according to the fluid transfer rule. In FIGS. 19-24, 'L' and 'H' indicate either low or high pressure, respectively, applied to a reservoir or node.

Figure 20:
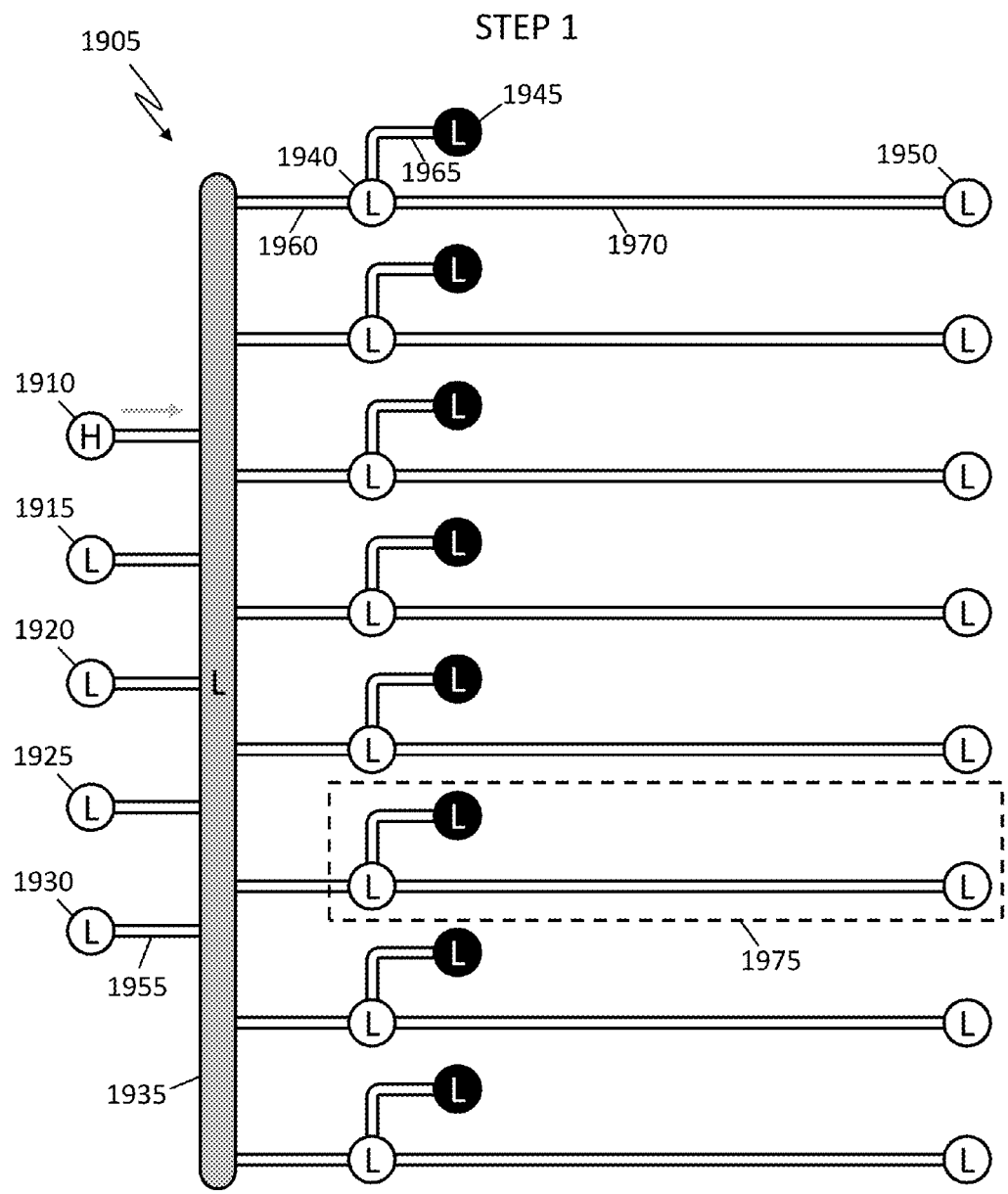
FIG. 20 is a diagram of a reconfigurable microfluidic device for multichannel immunoassays, seen in plan view.
Figure 21:
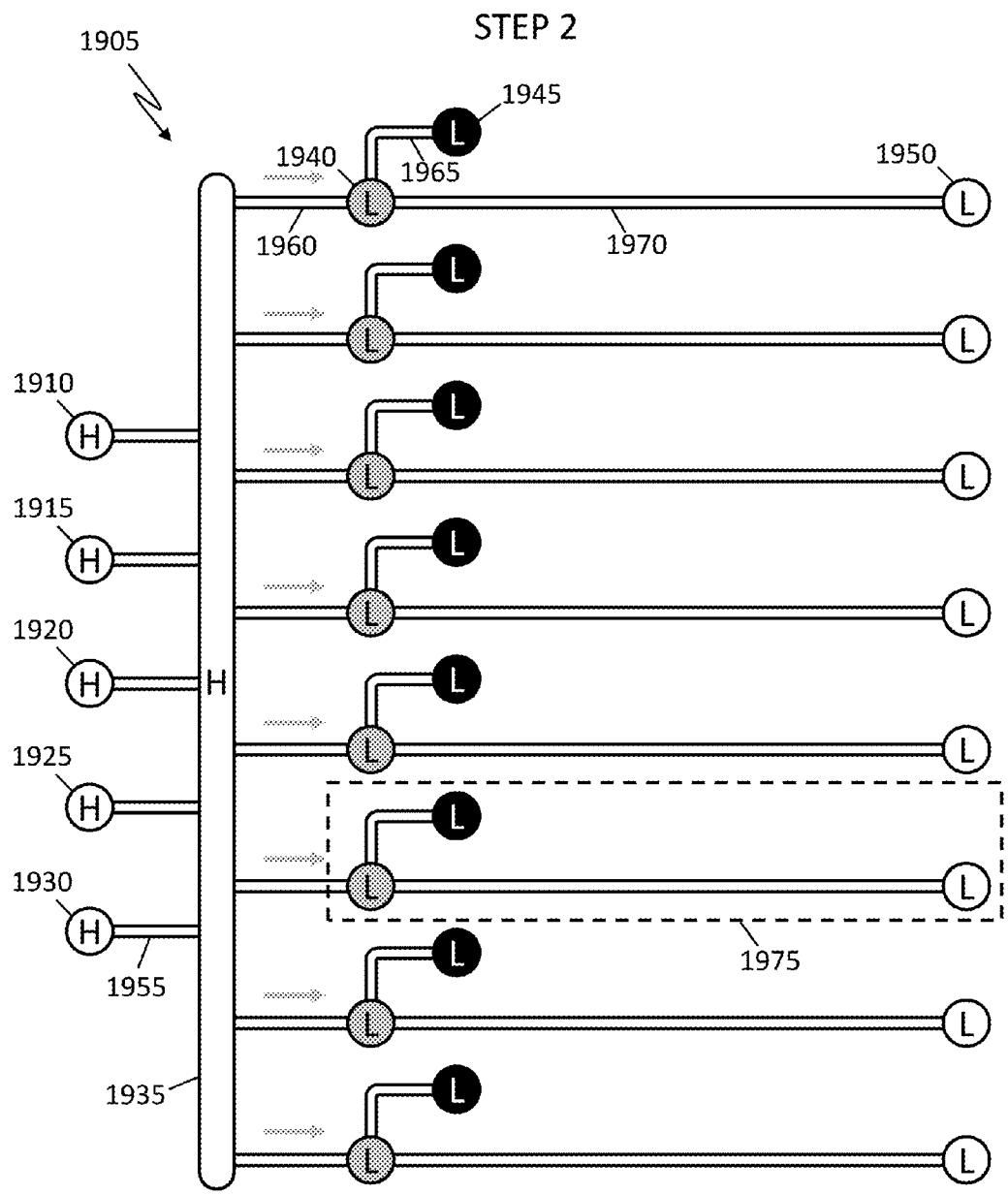
FIG. 21 is a diagram of a reconfigurable microfluidic device for multichannel immunoassays, seen in plan view.

FIG. 19, STEP 0, is the initial condition in which all reservoirs and nodes are at low pressure. Shading highlights the presence of fluid in reservoirs 1910 and 1945. Fluid is also present in the other, unnumbered reservoirs corresponding to reservoir 1945. In FIG. 20, STEP 1, fluid from reservoir 1910 is transferred to node 1935. In FIG. 21, STEP 2, fluid from node 1935 is transferred to node 1940 and to the other unnumbered nodes corresponding to node 1940.

Figure 22:
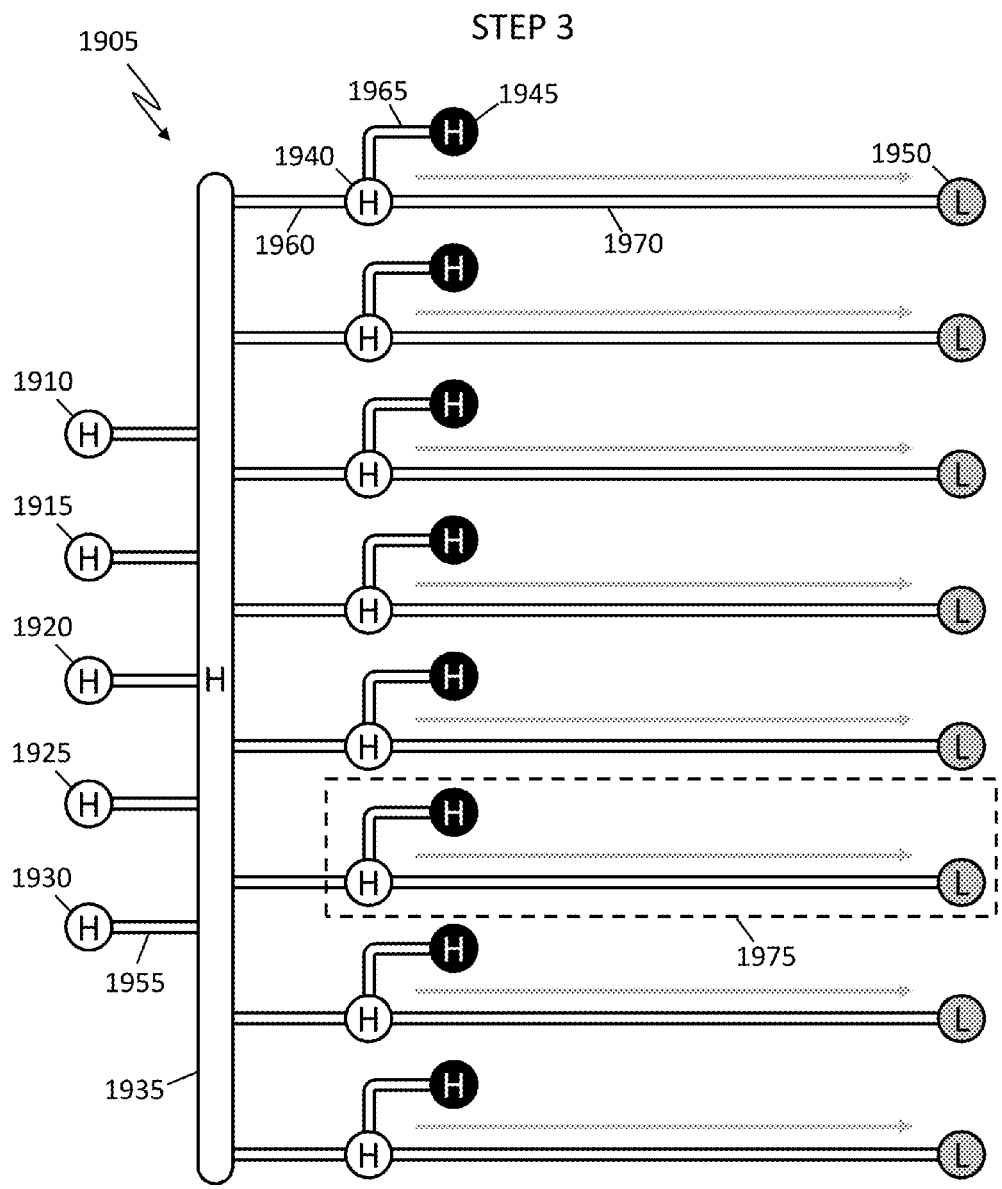
FIG. 22 is a diagram of a reconfigurable microfluidic device for multichannel immunoassays, seen in plan view.

In FIG. 22, STEP 3, fluid from node 1940 is transferred to reservoir 1950. Similar fluid transfer occurs simultaneously in each of the other immunoassay channels. In an immunoassay experiment, this step is completed in two stages: first, fluid is pushed from node 1940 into channel 1970 and allowed to incubate there; second the fluid is pushed into reservoir 1950. This procedure permits, for example, coating the walls of channel 1970 with antibodies or incubation of a sample with antibodies that have been chemically linked to the walls of the channel in a previous step.

In FIG. 23, STEP 4, sample solution from reservoir 1945 is transferred to node 1940. This same fluid movement occurs in each of the eight immunoassay channels, but the composition of the sample may be different in each one. In FIG. 24, STEP 5, the sample solution is transferred from node 1940 to reservoir 1950. As in STEP 3, this transfer is completed in two stages in an actual immunoassay, including incubation time in channel 1970. This same fluid movement occurs in each of the eight immunoassay channels. After STEP 5, fluid in reservoir 1950 and corresponding reservoirs may be tested, e.g., for optical absorption. Absorption may be measured while fluid is in device 1905 or fluid may be unloaded to an external container (a 96-well plate, for example) as discussed above in connection with FIG. 3.

Multichannel immunoassay device 1905 is a generalization of single-channel device 1105. It permits a particular immunoassay chemistry to be applied to many samples at once. Although device 1905 processes eight samples simultaneously, additional immunoassay channels may be included in a design to process even more samples.

Figure 25:
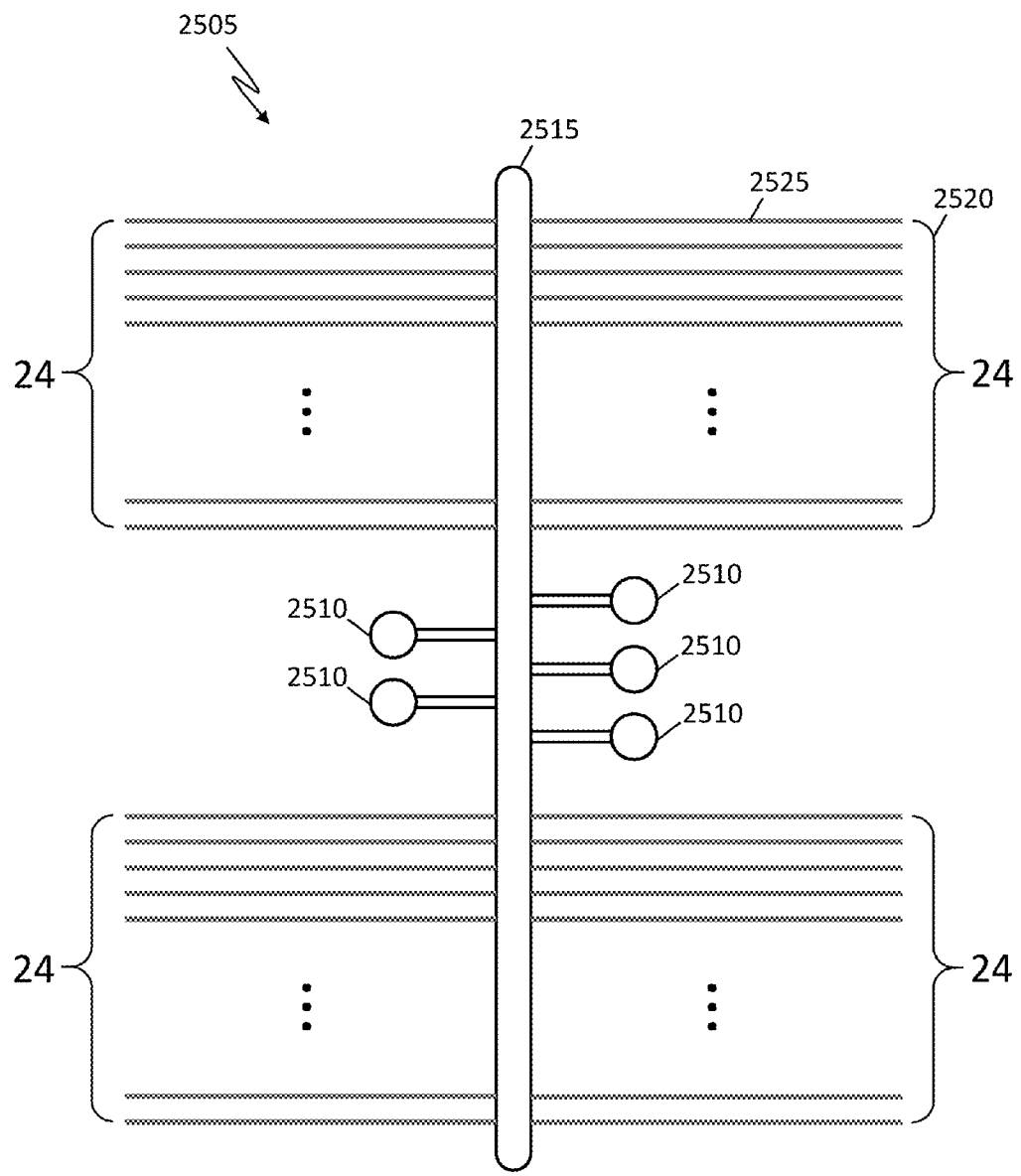
FIG. 25 is a conceptual diagram of a reconfigurable microfluidic device for 96-channel immunoassays.

For example, FIG. 25 is a conceptual diagram of a reconfigurable microfluidic device 2505 for 96-channel immunoassays. The 96-fluid-sample output of device 2505 may be loaded into a 96-well plate for analysis with a standard plate reader. FIG. 25 is schematic. In the figure, circles 2510 represent reservoirs that may contain wash buffers, enzymes, substrates, antibodies and blocking buffers, for example. These reservoirs are analogous to reservoirs 1910-1930 in FIGS. 19-24. Oval 2515 represents a reservoir that is analogous to reservoir 1935 in FIGS. 19-24. Braces 2520 denote groups of immunoassay channels such as 2525. These immunoassay channels are analogous to immunoassay channel 1975 in FIGS. 19-24. Each channel may be loaded with a unique sample. The large number "24" in FIG. 25 indicates that there are 24 immunoassay channels arranged in a group. Four such groups of 24 make 96 immunoassay channels in total. Of course, devices like 2505 may be designed with different numbers of immunoassay channels. Devices with 384 or 1536 channels may be constructed to be compatible with popular well plate configurations, for example.

One of the limitations of the multichannel immunoassay devices of FIGS. 19-25 is that each sample is loaded into the microfluidic device from an external "macrofluidic" system such as a pipette robot. This means that macroscopic sample volumes are required for each type of immunoassay. The multiplexed assay devices described below remove this limitation.

Once a sample is loaded into a multiplexed assay device, it can be tested in many, biochemically different immunoassays all on the same device. This means that a smaller starting sample volume is required when compared to the multichannel assays discussed above.

Multiplexed immunoassay devices include a microfluidic structure defined here as a "microfluidic switched interaction region". A microfluidic switched interaction region is a microfluidic channel connected at one of its ends to two input channels via a node. The interaction region is connected at its other end to two output channels via another node. The interaction region is "switched" because the action of nodes described above allows operation of the device such that fluid travels from one (but not the other) of the input channels to one (but not the other) of the output channels. The switching action of a node cannot be replicated with a single microfluidic valve. However a switched interaction region may be implemented with a more complicated arrangement of microvalves as discussed below.

Figure 26:
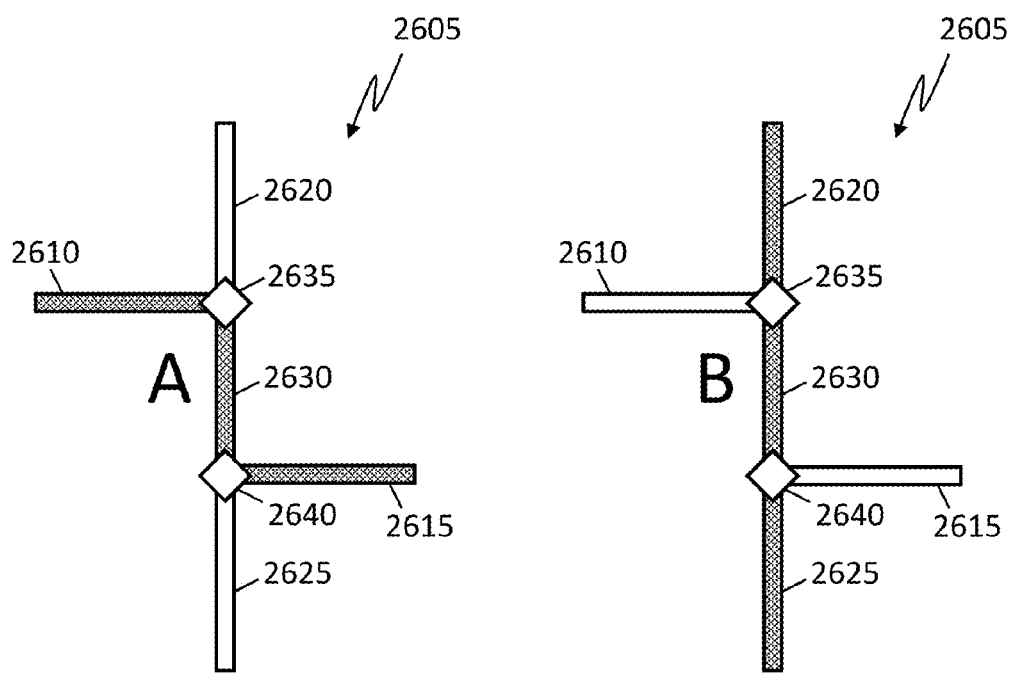
FIG. 26 illustrates a microfluidic switched interaction region.

FIG. 26 illustrates a microfluidic switched interaction region 2605 in two operational modes. At "A" an interaction region is operated such that fluid travels from one of its inputs to one of its outputs. At "B" the interaction region is operated such that fluid travels from the other input to the other output. Shading in the figure highlights these two modes. Fluid may also travel in the reverse direction, so "input" and "output" serve only as channel labels, not as indicators of flow direction.

In FIG. 26, input microfluidic channels 2610 and 2620 are connected to microfluidic channel 2630 via node 2635. Microfluidic channel 2635 is connected to output microfluidic channels 2615 and 2625 via node 2640.

Operation of the switched interaction region at "A" is as follows. Fluid from channel 2610 is accumulated in node 2635. Then the fluid is sent from node 2635 to node 2640. Finally the fluid is sent out via channel 2615. Fluid does not leak into channels 2620 or 2625, just as fluid did not leak into reservoir "C" in the fluid transfer experiment of FIGS. 4 and 5 discussed above. Operation of the switched interaction region at "B" is analogous, except that fluid arrives at node 2635 from channel 2620 and departs node 2640 via channel 2615.

Two other modes of operation are possible but not illustrated. Fluid may be switched from channel 2610 to 2625, or fluid may be switched from channel 2620 to 2615. These additional modes are not illustrated because they are analogous to modes "A" and "B", and they are not necessary to the discussion of multiplexed assays.

Figure 27:
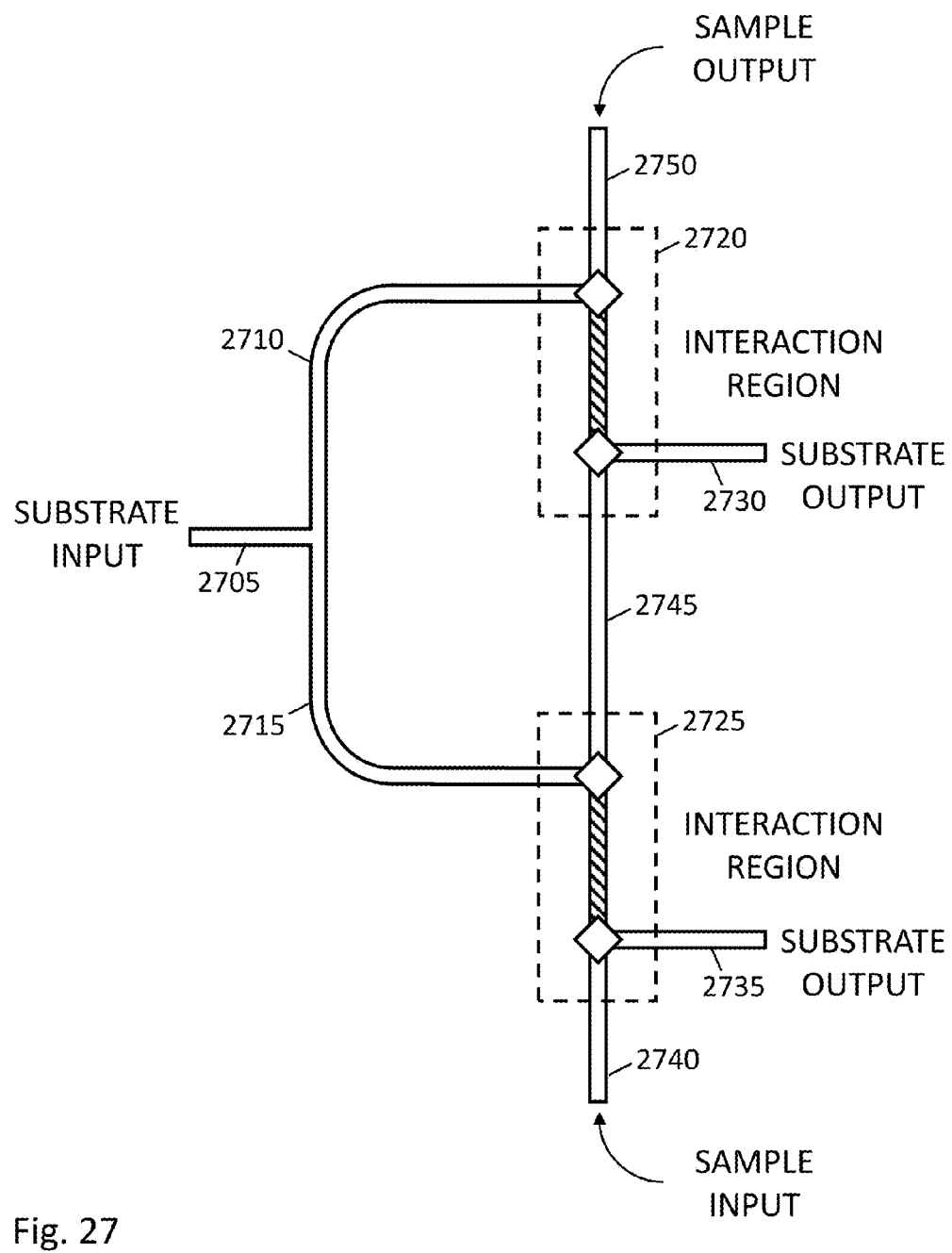
FIG. 27 illustrates multiple microfluidic switched interaction regions in series.

Multiplexed immunoassays are performed with reconfigurable microfluidic devices having multiple microfluidic switched interaction regions connected in series as illustrated in FIG. 27. FIG. 27 shows an example in which two switched interaction regions are connected in series. A system with three switched interaction regions in series is illustrated in FIGS. 28-33. In fact, systems may be designed with any number of switched interaction regions connected in series. When switched interaction regions are connected in series, an output channel of one interaction region is connected to an input channel of the next interaction region. All of the interaction regions may also be connected to a common input channel.

In a system like that of FIG. 27, one sample is processed in multiple interaction regions. Each interaction region supports an immunoassay with a different antibody. Thus one sample can be tested for the presence of many different antigens. The high specificity of antigen-antibody interactions permits the same sample to be processed in different immunoassays, simultaneously or one after the other. The same enzyme linked detection chemistry may be used in each interaction region because each interaction region has its own substrate output.

In FIG. 27, substrate input channel 2705 is split into two branches 2710 and 2715 which lead to interaction regions 2720 and 2725, respectively. Interaction regions 2720 and 2725 have the same structure as interaction region 2605 in FIG. 26. During normal immunoassay operations, interaction region 2720 either takes fluid input from channel 2710 and sends it out via channel 2730 or it takes fluid input from channel 2745 and sends it out via channel 2750. Similarly, interaction region 2725 either takes fluid input from channel 2715 and sends it out via channel 2735 or it takes fluid input from channel 2740 and sends it out via channel 2745.

The overall steps (ignoring rinses, buffers, etc.) for performing multiplexed immunoassays with a system like that of FIG. 27 are: coat each interaction region with a (possibly different) kind of antibodies; load a sample into the interaction regions and incubate; load substrate into the interaction regions; collect substrate from each interaction region separately; analyze collected substrates, e.g. by optical absorption. Alternatively, the sample can be loaded into one interaction region for incubation and then sent to subsequent interaction regions later. These steps are illustrated in FIGS. 28-33 which are diagrams of a reconfigurable microfluidic device for multiplexed immunoassays.

FIGS. 28-33 show a reconfigurable microfluidic device in plan view, like FIGS. 11-16 and FIGS. 19-24. The device includes reservoirs, nodes and channels, and it moves fluid via application of the fluid transfer rule. Since the fluid transfer rule has been explained and demonstrated in several examples above, FIGS. 28-33 do not include pressure labels such as "H" and "L". FIGS. 28-33 also omit some optional nodes which are described later in connection with FIG. 34. Furthermore, FIGS. 28-33 and associated description omit various rinsing, buffer and enzyme conjugate steps. Rather, the discussion of FIGS. 28-33 is directed to describing fluid movements that permit multiplexed immunoassays in a multiplexed immunoassay device. All such fluid movements may be accomplished via application of the fluid transfer rule and pressures may be applied at nodes and reservoirs automatically with a pressure sequencer such as that discussed above and shown in FIG. 9.

Figure 28:
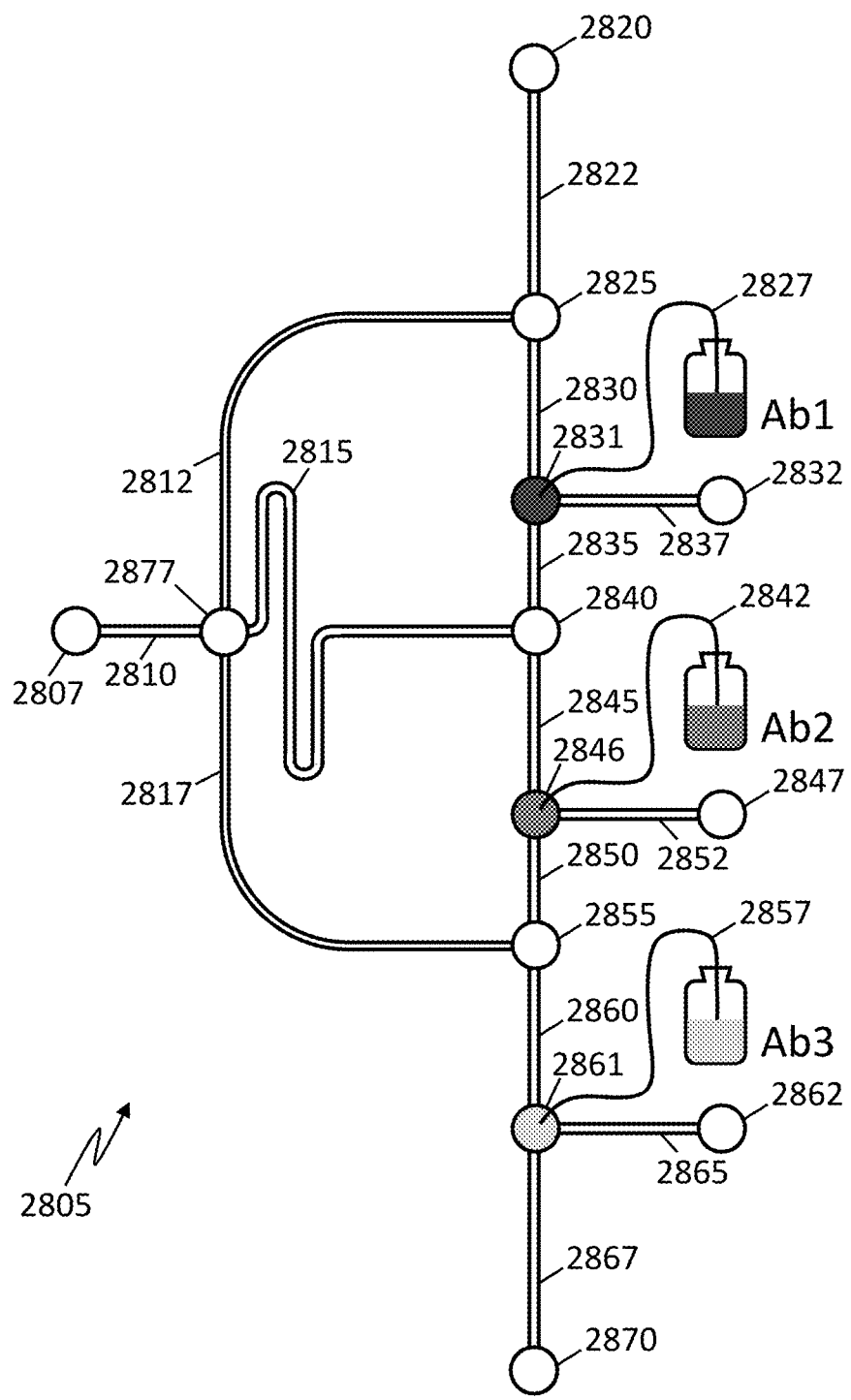
FIG. 28 is a diagram of a reconfigurable microfluidic device for multiplexed immunoassays.

In FIG. 28, reconfigurable microfluidic device 2805 includes reservoirs 2807, 2820, 2832, 2847, 2862, 2870, nodes 2825, 2831, 2840, 2846, 2855, 2861, 2877, and channels 2810, 2812, 2815, 2817, 2822, 2830, 2835, 2837, 2845, 2850, 2852, 2860, 2865, and 2867. Antibody supplies Ab1, Ab2 and Ab3 are connected to nodes 2831, 2846 and 2861 via supply tubes 2827, 2842 and 2857, respectively.

In FIG. 28, antibody solution from Ab1 is loaded into node 2831, antibody solution from Ab2 is loaded into node 2846, and antibody solution from Ab3 is loaded into node 2861. Antibody loading from the antibody supplies to the nodes may accomplished in the manner described above in connection with FIG. 2. This is an example of nodes temporarily storing fluid.

Figure 29:
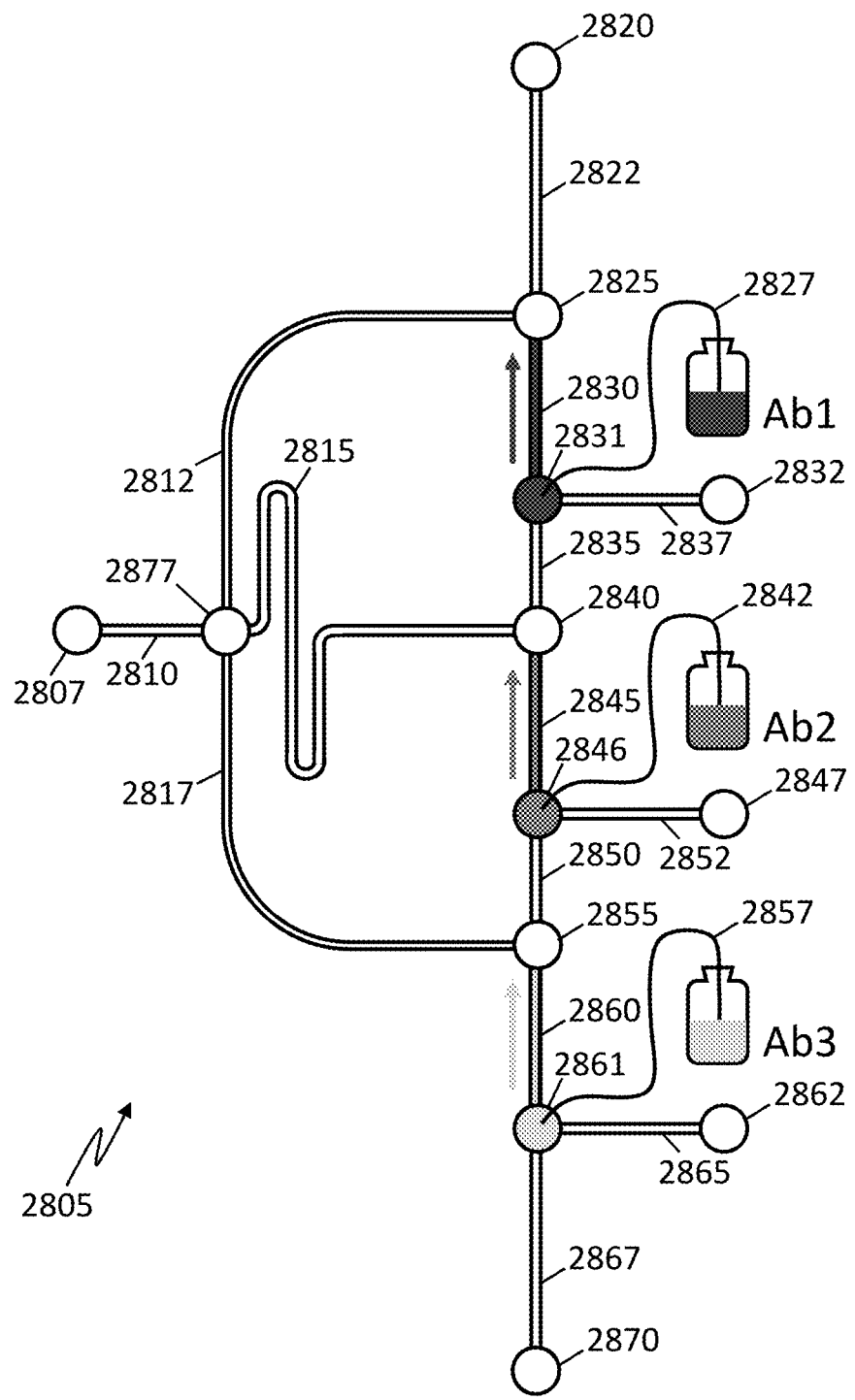
FIG. 29 is a diagram of a reconfigurable microfluidic device for multiplexed immunoassays.

In FIG. 29, antibodies from Ab1 are chemically linked to the walls of channel 2830, antibodies from Ab2 are chemically linked to the walls of channel 2845, and antibodies from Ab3 are chemically linked to the walls of channel 2860.

Figure 30:
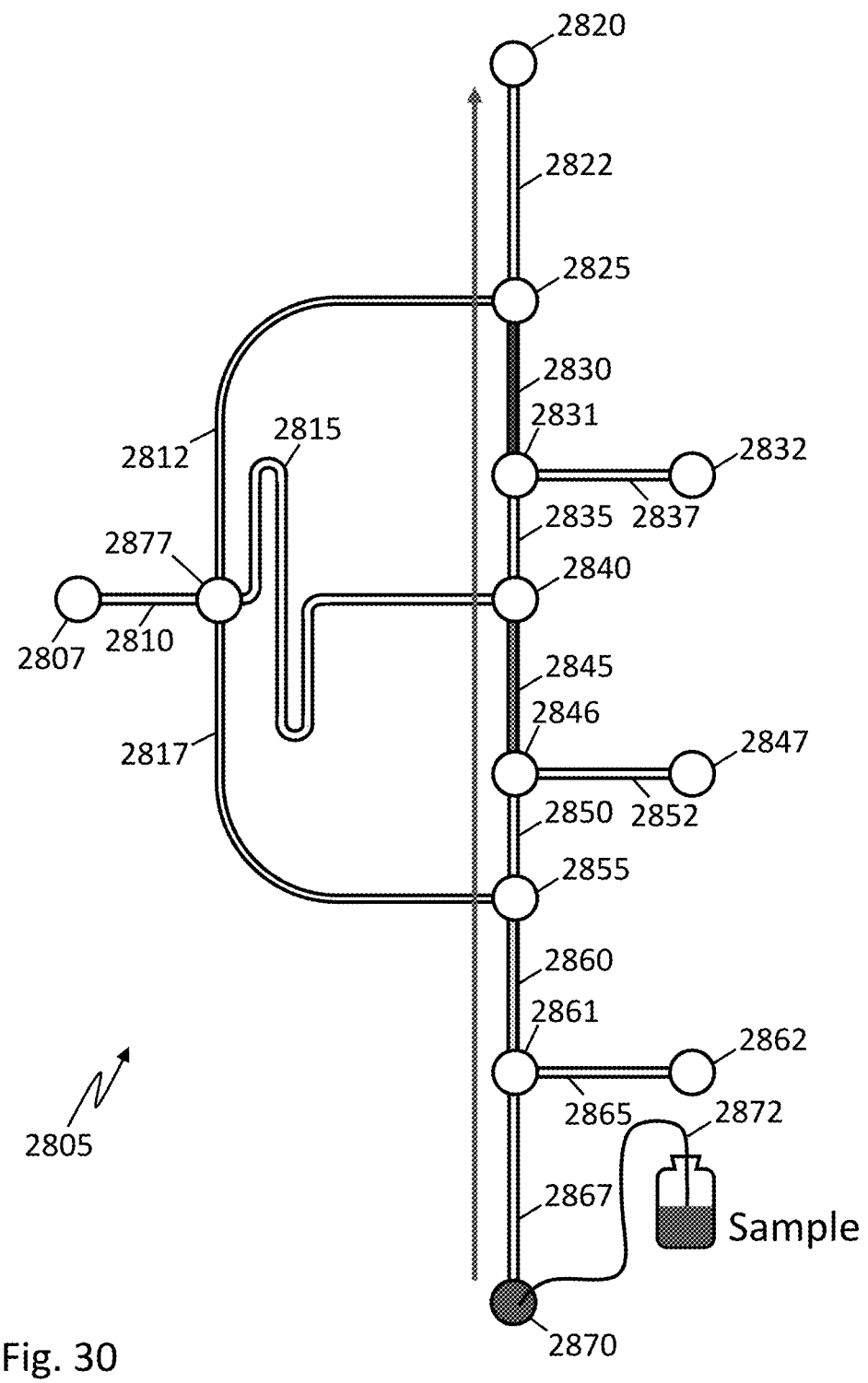
FIG. 30 is a diagram of a reconfigurable microfluidic device for multiplexed immunoassays.

In FIG. 30, sample solution from Sample supply is loaded into reservoir 2870 via supply tube 2872. After the sample solution is loaded in the reservoir it is sent through channels 2867, 2860, 2850, 2845, 2835, 2830 and 2822. The sample solution interacts with antibodies from antibody solutions Ab1, Ab2 and Ab3 in channels 2830, 2845 and 2860, respectively. Sample solution may be distributed in all three interaction regions (2830, 2845 and 2860) at once for simultaneous immunoassays, or it may be first kept in one interaction region and later sent to other interaction regions for sequential immunoassays. Antibodies do not move from one interaction region to another because they are chemically linked to the walls of channels 2830, 2845 and 2860.

Figure 31:
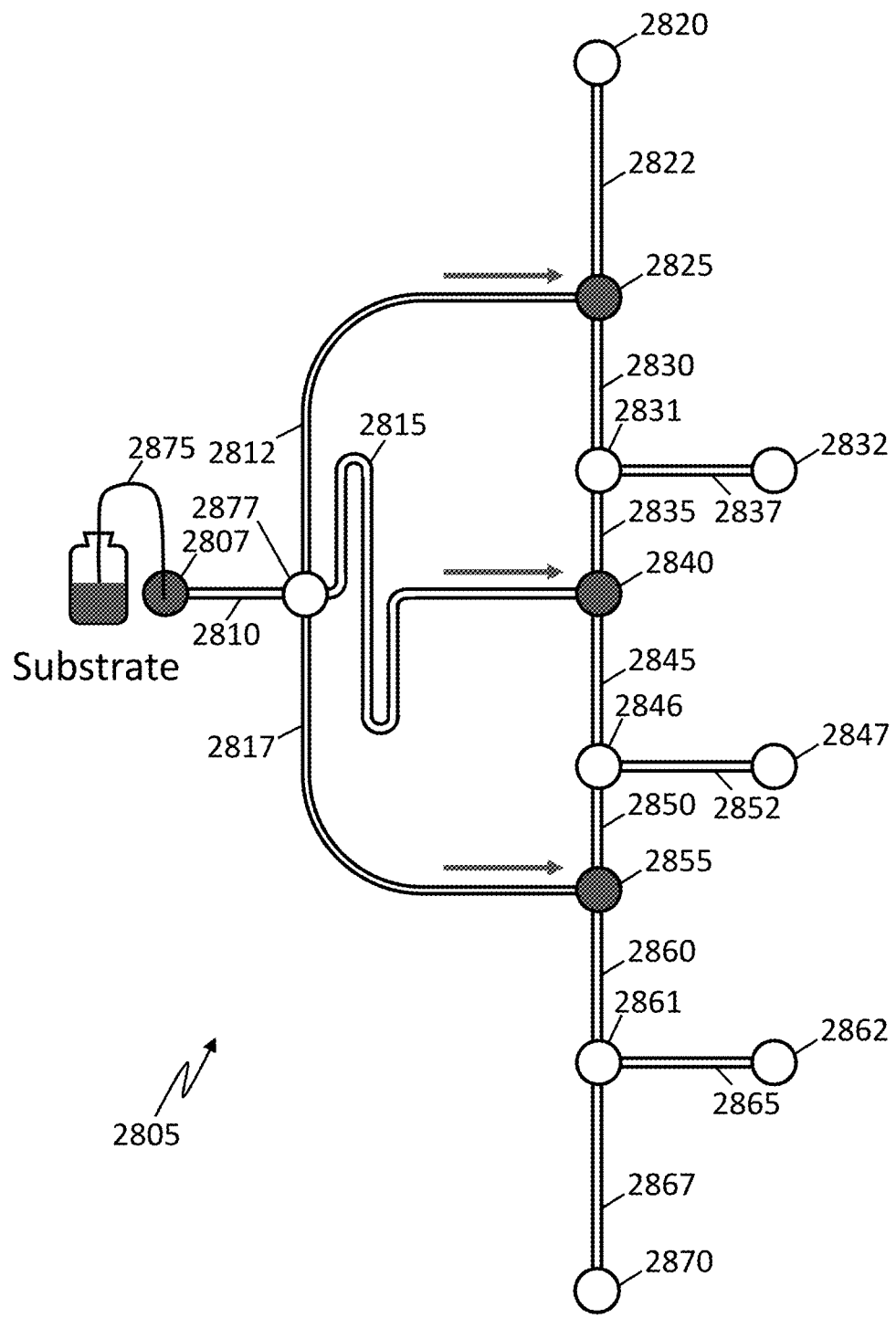
FIG. 31 is a diagram of a reconfigurable microfluidic device for multiplexed immunoassays.

In FIG. 31, substrate solution from Substrate supply is loaded into reservoir 2807 via supply tube 2875. Substrate solution is then moved to node 2877 and on to nodes 2825, 2840 and 2855 via channels 2812, 2815 and 2817, respectively. Channels 2812, 2815 and 2817 may be designed to have the same length. Alternatively, substrate solution may loaded into node 2877; the substrate solution may then be sent to nodes 2825, 2840 and 2855 sequentially, if desired.

Figure 32:
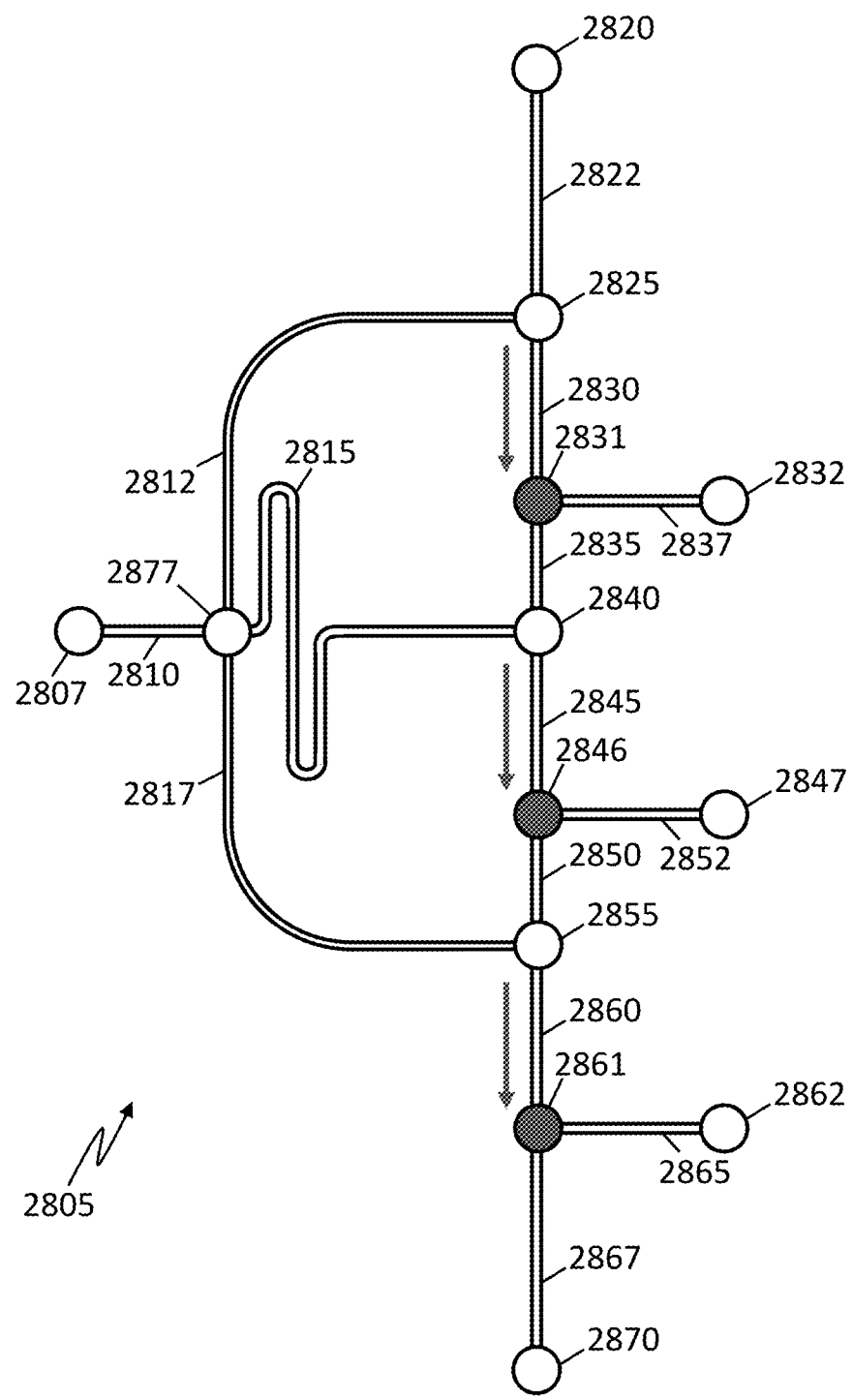
FIG. 32 is a diagram of a reconfigurable microfluidic device for multiplexed immunoassays.

In FIG. 32, substrate solution is moved from node 2825 to node 2831, from node 2840 to node 2846, and from node 2855 to node 2861, after interacting with antigen-antibody complexes in channels 2830, 2845 and 2860 respectively.

Figure 33:
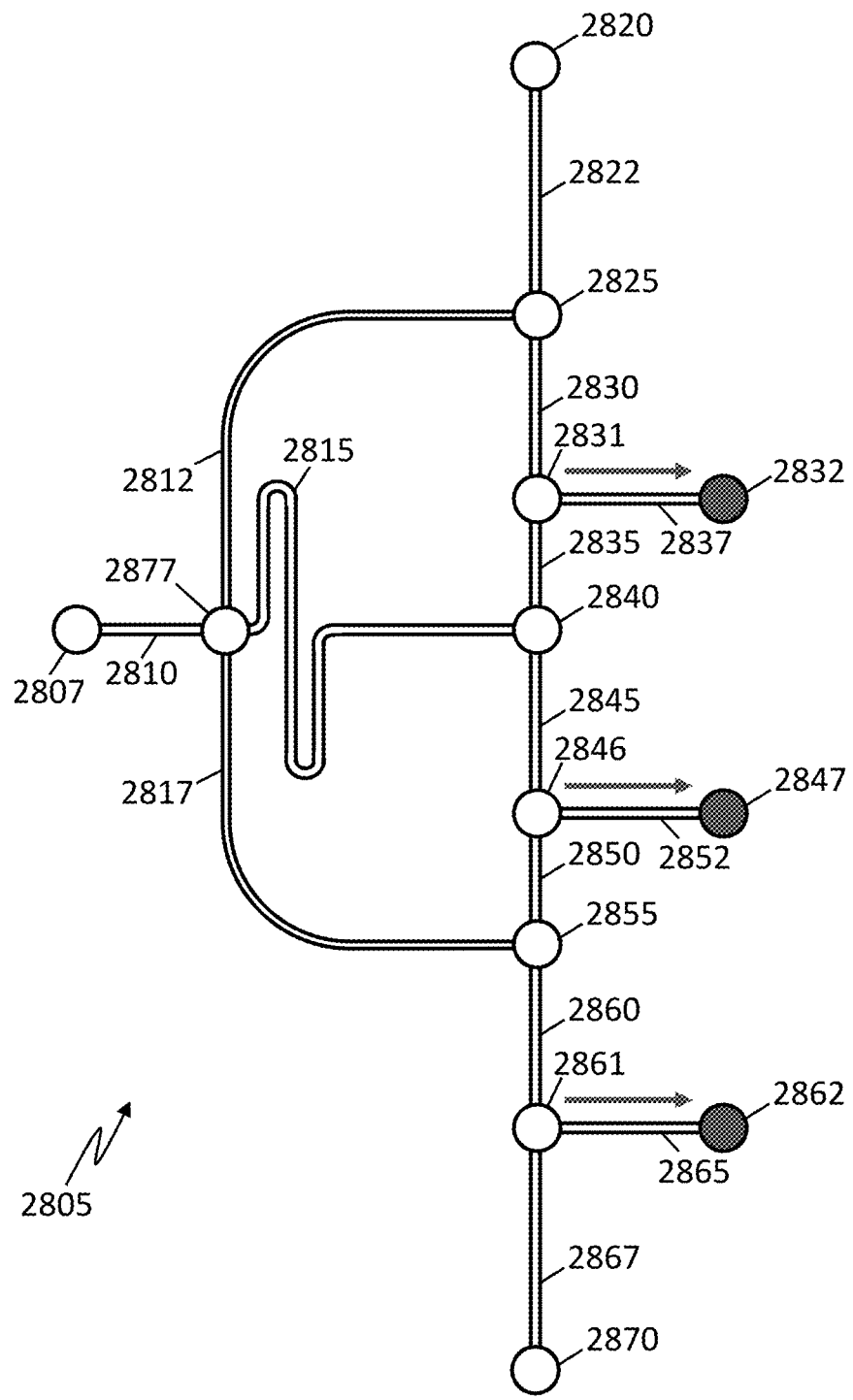
FIG. 33 is a diagram of a reconfigurable microfluidic device for multiplexed immunoassays.

Finally in FIG. 33, substrate solution is moved from nodes 2831, 2846 and 2861 to reservoirs 2832, 2847 and 2862 respectively. Here the solution may be unloaded (as in FIG. 3, for example) for optical absorption analysis.

Device 2805, based on multiple microfluidic switched interaction regions connected in series, permits one sample solution to interact with different kinds of antibodies that are linked to the walls of different microfluidic channels. Detection of antigen-antibody interactions is then performed separately in each of those channels. This is helpful for immunoassays because only a limited number of different enzyme-linked detection protocols are known, with one based on HRP cleaving TMB being the most common.

Device 2805 has three interaction regions for testing a sample with as many as three different kinds of antibodies. However, the device can be extended for operation with more different kinds of antibodies by adding more microfluidic switched interaction regions in series.

Figure 34:
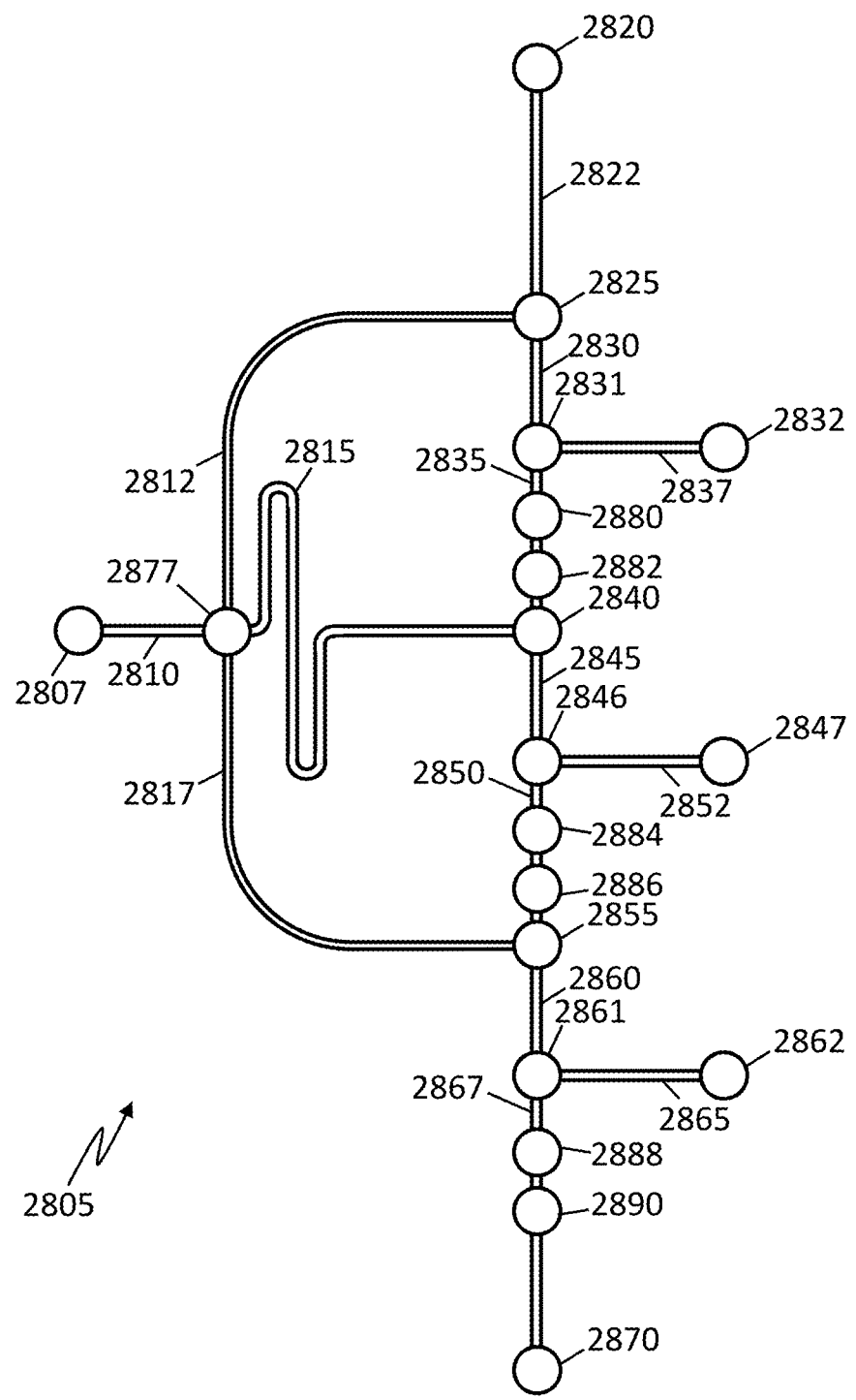
FIG. 34 shows the reconfigurable microfluidic device of FIGS. 28-33 with the addition of optional nodes.

FIG. 34 shows the reconfigurable microfluidic device of FIGS. 28-33 with the addition of optional nodes 2880, 2882, 2884, 2886, 2888 and 2890. These optional nodes, or "buffer nodes", permit fully parallel operation of device 2805 for antibody and substrate loading into interaction regions. FIGS. 29 and 32 discussed above illustrate operations in which fluid flows in the three interaction regions of device 2805. However, when only the nodes shown in those figures are present, the fluid flows in the interaction regions must occur sequentially, not at the same time. (Other fluid flows, outside the interaction regions, may occur simultaneously.)

As an example, consider coating channel 2830 with Ab1 in FIG. 29. This is accomplished by setting node 2831 to high pressure and node 2825 to low pressure. If the same operations were performed at the same time with channel 2845 and nodes 2846 and 2840, then fluid would also travel from node 2831 to node 2840 (low pressure). In FIG. 34, buffer node 2880, set to high pressure, and buffer node 2882, set to low pressure, prevent the undesired flow of fluid from node 2831 to node 2840 during this operation.

A similar situation exists in the scenario of FIG. 32 when substrate solution is moved from node 2825 to node 2831 (and from 2840 to 2846, and from 2855 to 2861). In FIG. 34, buffer node 2880 is set to low pressure and buffer node 2882 is set to high pressure to prevent undesired flow of fluid from node 2840 to node 2831. In all cases, buffer node 2880 is set to the same pressure as node 2831 and buffer node 2882 is set to the same pressure as node 2840. Similarly, buffer node 2884 may always be set to the same pressure as node 2846 and buffer node 2886 may always be set to the same pressure as node 2855, etc.

Optional buffer nodes 2880, 2882, 2884, 2886, 2888 and 2890 therefore prevent simultaneous fluid flows in the series-connected interaction regions from contaminating each other. This is not a required capability for multiplexed immunoassays, as fluid flows in the interaction regions may be performed sequentially. However, simultaneous operation also reduces the complexity of node pressure sequencing. When the optional buffer nodes are present, the pressures at, for example, nodes 2825 and 2840, may always be set equal to each other, both high or both low, and therefore they may be supplied from a common pressure tube or pressure manifold. This reduces the number of pressure tubes and external pressure sources needed.

Figure 35:
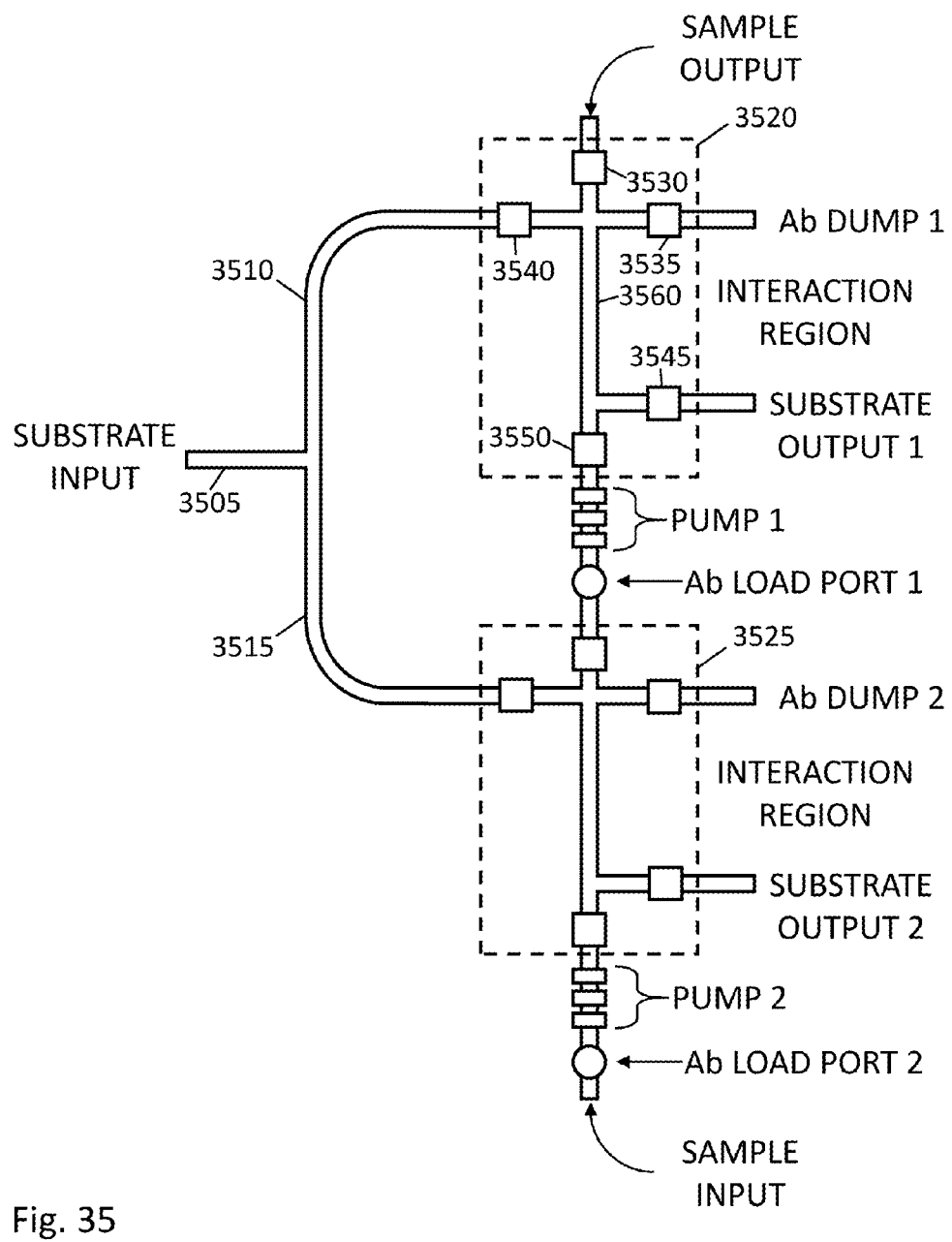
FIG. 35 is a diagram of a microfluidic device for multiplexed immunoassays based on microvalves.

Immunoassay devices with microfluidic switched interaction regions may also be implemented with microfluidic valves as shown in FIG. 35. FIG. 35 may be compared to FIGS. 26 and 27. FIGS. 27 and 35 show microfluidic devices having multiple microfluidic switched interaction regions connected in series. However, the device of FIG. 35 is implemented with conventional microvalves while the device of FIG. 27 is implemented with reservoirs and nodes. A microvalve is a microfluidic device that opens and closes to allow or prevent fluid flow past the microvalve in a microfluidic channel. Microvalves considered here may be of any conventional design, such as normally-open microvalves or normally-closed microvalves.

In FIG. 35, substrate input channel 3505 is split into two branches 3510 and 3515 which lead to interaction regions 3520 and 3525, respectively. Interaction regions 3520 and 3525 include the same structure as interaction region 2605 in FIG. 26. However, in FIG. 35 the interaction regions are based on microvalves and further include an extra dump port.

During normal immunoassay operations, interaction region 3520 may route fluid input from channel 3510 to SUBSTRATE OUTPUT 1; or it may route fluid input from PUMP 1 to SAMPLE OUTPUT; or it may route fluid from PUMP 1 to Ab DUMP 1. Similarly, interaction region 3525 either routes fluid input from channel 3515 to SUBSTRATE OUTPUT 2; or it routes fluid input from PUMP 2 to SAMPLE OUTPUT (via interaction region 3520); or it routes fluid from PUMP 2 to Ab DUMP 2.

Dump ports Ab DUMP 1 and Ab DUMP 2 are needed because a microvalve-based system does not include nodes that can temporarily store fluid. When PUMP 1 operates to coat antibodies supplied at Ab LOAD PORT 1 on the walls of channel 3560, the fluid already in that channel must be provided with somewhere to go—dump port Ab DUMP 1, in this case.

Interaction region 3520 serves as an example of a microvalve implementation of a microfluidic switched interaction region. Interaction region 3520 includes microvalves 3530, 3535, 3540, 3545, 3550 and channel 3560.

To route fluid from channel 3510 to SUBSTRATE OUTPUT 1, microvalves 3540 and 3545 are opened and microvalves 3530, 3535 and 3550 are closed. To route fluid from PUMP 1 to SAMPLE OUTPUT, microvalves 3530 and 3550 are opened and microvalves 3535, 3540 and 3545 are closed. To route fluid from PUMP 1 to Ab DUMP 1, microvalves 3535 and 3550 are opened and microvalves 3530, 3540 and 3545 are closed.

Interaction regions based on microvalves, connected in series, can perform the functions of a node-based device, such as shown in FIG. 27. In particular, the devices of FIGS. 27 and 35 both: (a) permit a single sample solution to interact with multiple interaction regions; and (b) permit antigen detection (via substrate interactions) in each interaction region separately. The devices of FIGS. 34 and 35 permit simultaneous fluid flows in all of their interaction regions.

PUMP 1 and PUMP 2 in FIG. 35 are microfluidic pumps which may be implemented as a series of three microfluidic valves each. Ab LOAD PORT 1 and Ab LOAD PORT 2 are ports via which antibodies may be loaded into the microfluidic system. SAMPLE INPUT is a port via which a sample may be loaded into the microfluidic system.

Multiplexed immunoassay devices based on multiple microfluidic switched interaction regions permit a single small-volume sample to be tested in many different immunoassays. Detection of different antigens in the sample is performed in different interaction regions; hence, the detection mechanism may be the same in each interaction region. Multiplexed assays may be scaled to analyze multiple samples across multiple immunoassays in systems containing many copies of a devices such as those illustrated in FIGS. 27-35.

The above description of the disclosed embodiments is provided to enable any person skilled in the art to make or use the invention. Various modifications to these embodiments will be readily apparent to those skilled in the art, and the principles defined herein may be applied to other embodiments without departing from the scope of the disclosure. Thus, the disclosure is not intended to be limited to the embodiments shown herein but is to be accorded the widest scope consistent with the principles and novel features disclosed herein.

What is claimed is:

1. A reconfigurable microfluidic system comprising:
two or more microfluidic switched interaction regions connected in series such that an output channel of one interaction region is connected to an input channel of the next interaction region, wherein each interaction region includes:
a hydrophobic microfluidic channel having a first end connected to two hydrophobic microfluidic input channels via a first microfluidic cavity and a second end connected to two hydrophobic microfluidic output channels via a second microfluidic cavity, the hydrophobic microfluidic channels have a higher resistance to fluid flow than that of the first or second microfluidic cavities, and each of the cavities includes a gas pressure port.

2. The reconfigurable microfluidic system of claim 1, wherein a plurality of the two or more microfluidic switched interaction regions are also connected to a common microfluidic input channel.

3. The reconfigurable microfluidic system of claim 1, wherein, in each interaction region, the hydrophobic microfluidic channels have a resistance to fluid flow at least 100 times greater than that of the cavities.

4. The reconfigurable microfluidic system of claim 1, wherein, in each interaction region, the hydrophobic microfluidic channels have a resistance to fluid flow at least 1,000 times greater than that of the cavities.

5. The reconfigurable microfluidic system of claim 1, wherein, in each interaction region, the hydrophobic microfluidic channels have a resistance to fluid flow at least 10,000 times greater than that of the cavities.

6. The reconfigurable microfluidic system of claim 1, wherein, in each interaction region, the cavities are formed in a hydrophobic microfluidic layer that is bonded to a substrate layer, and the cavities are sealed by a pneumatic layer that is bonded to the microfluidic layer.

7. The reconfigurable microfluidic system of claim 6, wherein the microfluidic layer is made from polydimethylsiloxane.

8. The reconfigurable microfluidic system of claim 6, wherein the microfluidic layer is made from fluorinated ethylene propylene.

9. The reconfigurable microfluidic system of claim 6, wherein the microfluidic layer is made from polytetrafluoroethylene.

10. The reconfigurable microfluidic system of claim 6, wherein the pneumatic layer includes a gas manifold that acts as a pressure port for two or more cavities.

11. The reconfigurable microfluidic system of claim 1 further comprising fluid tubing connecting at least one cavity in at least one interaction region to an external fluid store maintained at atmospheric pressure.

12. The reconfigurable microfluidic system of claim 1 further comprising gas tubing connecting at least one cavity in at least one interaction region to a gas pressure source.

13. The reconfigurable microfluidic system of claim 1, wherein at least one microfluidic channel has a gas pressure port.

14. The reconfigurable microfluidic system of claim 1 further comprising a pressure sequencer including a set of gas valves, the pressure sequencer connected by gas tubing to: a high pressure gas source, a low pressure gas source, and to at least one cavity.

15. The reconfigurable microfluidic system of claim 14, wherein the pressure sequencer applies high gas pressure and low gas pressure to the at least one cavity according to pressure sequence data.

16. The reconfigurable microfluidic system of claim 15, wherein the hydrophobic microfluidic channels of each interaction region have a hydrophobic pressure barrier to fluid flow that is less than the pressure difference between the high gas pressure and the low gas pressure.

17. The reconfigurable microfluidic system of claim 16, wherein the pressure sequence data follow a fluid transfer rule in which high gas pressure is applied to an origin cavity from which a fluid is transferred and low gas pressure is applied to a destination cavity to which the fluid is transferred, and high gas pressure is applied to any cavity (other than the destination cavity) connected to the origin cavity by a channel and low gas pressure is applied to any cavity (other than the origin cavity) connected to the destination cavity by a channel, and where high gas pressure is a pressure greater than low gas pressure.

18. A method for performing a multiplexed immunoassay, the method comprising:
providing sample analyte, capture analyte and detection reagent, and operating the reconfigurable microfluidic system of claim 17 according to pressure sequence data such that the pressure sequencer directs fluid flows in the system that cause different kinds of sample-analyte-capture-analyte reactions to occur in different interaction regions, but the same kind of detection reagent reaction to occur in a plurality of interaction regions.

19. The method of claim 18 wherein the sample-analyte-capture-analyte reactions are antibody-antigen reactions.

20. The method of claim 18 wherein the detection reagent reaction is an enzyme-linked detection reaction.

21. The method of claim 18 wherein the pressure sequencer directs fluid flows via which capture analyte solutions are loaded into a plurality of interaction regions simultaneously.

22. The method of claim 18 wherein the pressure sequencer directs fluid flows via which detection reagent solution in loaded into a plurality of interaction regions simultaneously.

23. The method of claim 18 wherein the pressure sequencer directs fluid flows via which sample analyte solution is incubated a plurality of interaction regions simultaneously.

24. The method of claim 18 wherein the pressure sequencer directs fluid flows via which sample analyte solution is incubated a plurality of interaction regions sequentially.

* * * * *